(12) United States Patent
Li et al.

(10) Patent No.: US 12,163,193 B2
(45) Date of Patent: Dec. 10, 2024

(54) BIOMARKERS FOR CANCER THERAPY

(71) Applicant: Beijing Percans Oncology Co., Ltd., Beijing (CN)

(72) Inventors: Xiang Li, Beijing (CN); Yiyou Chen, San Jose, CA (US)

(73) Assignee: Beijing Percans Oncology Co., Ltd., Beijing (CN)

( * ) Notice: Subject to any disclaimer, the term of this patent is extended or adjusted under 35 U.S.C. 154(b) by 801 days.

(21) Appl. No.: 17/268,042

(22) PCT Filed: Aug. 12, 2019

(86) PCT No.: PCT/US2019/046124
§ 371 (c)(1),
(2) Date: Feb. 11, 2021

(87) PCT Pub. No.: WO2020/036852
PCT Pub. Date: Feb. 20, 2020

(65) Prior Publication Data
US 2021/0180141 A1 Jun. 17, 2021

(30) Foreign Application Priority Data

Aug. 13, 2018 (WO) ................ PCT/CN2018/100206
Nov. 6, 2018 (WO) ................ PCT/CN2018/115826

(51) Int. Cl.
*C12Q 1/6886* (2018.01)
*A61K 31/497* (2006.01)
(Continued)

(52) U.S. Cl.
CPC .......... *C12Q 1/6886* (2013.01); *A61K 31/497* (2013.01); *A61K 45/06* (2013.01);
(Continued)

(58) Field of Classification Search
CPC ............ C12Q 1/6886; C12Q 2600/106; C12Q 2600/156; A61P 35/00; A61K 31/497; A61K 45/06
See application file for complete search history.

(56) References Cited

U.S. PATENT DOCUMENTS 5,844,093 A 12/1998 Kettleborough et al.
6,734,203 B2 5/2004 Matsuhisa et al.
(Continued)

FOREIGN PATENT DOCUMENTS

CA 2 943 402 A1 10/2015
CN 1400969 A 3/2003
(Continued)

OTHER PUBLICATIONS

Asahi J. Med. Oncl. Ther 2016; 1(2):62-71 (Year: 2016).*
(Continued)

*Primary Examiner* — Clinton A Brooks
*Assistant Examiner* — Jerica Katlynn Wilson
(74) *Attorney, Agent, or Firm* — COOLEY LLP

(57) ABSTRACT

Provided are methods of using a MYC gene as a biomarker for predicting therapeutic efficacy of survivin inhibitors such as YM155 monobromide in cancer therapy, and related kits, compositions, and methods for diagnosing and treating cancer in a subject in need thereof.

9 Claims, 14 Drawing Sheets

(51) Int. Cl.
  *A61K 45/06* (2006.01)
  *A61P 35/00* (2006.01)
(52) U.S. Cl.
  CPC ........ *A61P 35/00* (2018.01); *C12Q 2600/106* (2013.01); *C12Q 2600/156* (2013.01)

(56) References Cited

U.S. PATENT DOCUMENTS

| | | |
|---|---|---|
| 7,132,511 B2 | 11/2006 | Carr et al. |
| 7,247,301 B2 | 7/2007 | van de Winkel et al. |
| 7,595,378 B2 | 9/2009 | van de Winkel et al. |
| 7,618,992 B2 | 11/2009 | Nakahara et al. |
| 7,723,484 B2 | 5/2010 | Beidler et al. |
| 7,939,072 B2 | 5/2011 | Yarden et al. |
| 7,960,516 B2 | 6/2011 | Matheus et al. |
| 8,003,105 B2 | 8/2011 | Nakahara et al. |
| 9,662,329 B2 | 5/2017 | Chang et al. |
| 9,737,535 B2 | 8/2017 | Fultz et al. |
| 10,004,735 B2 | 6/2018 | Fultz et al. |
| 2003/0114508 A1 | 6/2003 | Matsuhisa et al. |
| 2005/0222163 A1 | 10/2005 | Eck et al. |
| 2006/0223831 A1 | 10/2006 | Kinoyama et al. |
| 2006/0257895 A1 | 11/2006 | Pinkel et al. |
| 2008/0166344 A1 | 7/2008 | Nakahara et al. |
| 2008/0280844 A1 | 11/2008 | Lessnick |
| 2009/0124595 A1 | 5/2009 | Adams et al. |
| 2009/0246198 A1 | 10/2009 | Dong et al. |
| 2009/0263390 A1 | 10/2009 | Nakahara et al. |
| 2010/0004234 A1 | 1/2010 | Santi et al. |
| 2010/0249413 A1 | 9/2010 | Murai et al. |
| 2012/0028907 A1* | 2/2012 | Shackney ............ C12Q 1/6886 544/405 |
| 2012/0122910 A1 | 5/2012 | Berezov et al. |
| 2013/0035336 A1 | 2/2013 | Borland et al. |
| 2013/0287772 A1 | 10/2013 | Halbert et al. |
| 2014/0199236 A1 | 7/2014 | Chen et al. |
| 2014/0271634 A1 | 9/2014 | Sliwkowski et al. |
| 2014/0314749 A1 | 10/2014 | French et al. |
| 2015/0086535 A1 | 3/2015 | Chang et al. |
| 2015/0185223 A1 | 7/2015 | Mano et al. |
| 2016/0024591 A1 | 1/2016 | Xu et al. |
| 2016/0095942 A1 | 4/2016 | Markovic et al. |
| 2016/0228457 A1 | 8/2016 | Chigaev et al. |
| 2016/0317538 A1 | 11/2016 | Saha et al. |
| 2016/0367663 A1 | 12/2016 | Doshi et al. |
| 2017/0027951 A1 | 2/2017 | Klampfer |
| 2017/0080093 A1 | 3/2017 | Hoffman |
| 2017/0114098 A1 | 4/2017 | Aivado et al. |
| 2017/0351837 A1 | 12/2017 | Donovan et al. |
| 2019/0046529 A1 | 2/2019 | Quayle et al. |
| 2019/0292602 A1 | 9/2019 | Chapuy et al. |
| 2020/0054635 A1 | 2/2020 | Campbell et al. |
| 2020/0147211 A1 | 5/2020 | Zhang et al. |
| 2021/0179718 A1 | 6/2021 | Chen et al. |
| 2023/0065640 A1 | 3/2023 | Li et al. |
| 2023/0104800 A1 | 4/2023 | Li et al. |
| 2023/0277536 A1 | 9/2023 | Guo |
| 2023/0357861 A1 | 11/2023 | Li |

FOREIGN PATENT DOCUMENTS

| | | |
|---|---|---|
| CN | 1791595 A | 6/2006 |
| CN | 106456774 A | 2/2017 |
| CN | 106822905 A | 6/2017 |
| CN | 107708734 A | 2/2018 |
| EP | 1614686 A1 | 1/2006 |
| EP | 1747784 A1 | 1/2007 |
| EP | 2 127 652 A1 | 12/2009 |
| EP | 2609920 A1 | 7/2013 |
| EP | 4100036 A1 | 12/2022 |
| JP | 2016104703 A | 6/2016 |
| JP | 2017502013 A | 1/2017 |
| JP | 2017511341 A | 4/2017 |
| KR | 20140131827 A | 11/2014 |
| WO | WO 01/60803 A1 | 8/2001 |
| WO | WO 2004/092160 A1 | 10/2004 |
| WO | WO-2007086342 A1 | 8/2007 |
| WO | WO 2007/140222 A2 | 12/2007 |
| WO | WO-2008032084 A1 | 3/2008 |
| WO | WO 2008/023807 A1 | 1/2010 |
| WO | WO 2010/020675 A1 | 2/2010 |
| WO | WO 2008/081927 A1 | 4/2010 |
| WO | WO-2010093465 A1 | 8/2010 |
| WO | WO-2010100899 A1 | 9/2010 |
| WO | WO 2012/161177 A1 | 11/2012 |
| WO | WO 2012/167099 A1 | 12/2012 |
| WO | WO-2013034806 A1 | 3/2013 |
| WO | WO-2013074596 A1 | 5/2013 |
| WO | WO 2013/148649 A1 | 10/2013 |
| WO | WO 2014/147573 A3 | 9/2014 |
| WO | WO-2014142220 A1 | 9/2014 |
| WO | WO-2015095840 A1 | 6/2015 |
| WO | WO-2015150826 A1 | 10/2015 |
| WO | WO 2016/191296 A1 | 12/2016 |
| WO | WO 2016/201370 A1 | 12/2016 |
| WO | WO-2017019279 A1 | 2/2017 |
| WO | WO 2017/037576 A1 | 3/2017 |
| WO | WO-2017048800 A1 | 3/2017 |
| WO | WO 2017/070475 A1 | 4/2017 |
| WO | WO 2017/120439 A1 | 7/2017 |
| WO | WO 2018/127786 A1 | 7/2018 |
| WO | WO 2020/034061 A1 | 2/2020 |
| WO | WO 2020/036852 A1 | 2/2020 |
| WO | WO 2020/097901 A1 | 5/2020 |
| WO | WO-2020181386 A1 | 9/2020 |
| WO | WO-2021155580 A1 | 8/2021 |
| WO | WO-2021155581 A | 8/2021 |
| WO | WO-2021262962 A1 | 12/2021 |
| WO | WO-2023044366 A1 | 3/2023 |

OTHER PUBLICATIONS

Schafer et al. Drug Discovery Today 2008, 13 (21/22), 913-916 (Year: 2008).*
Horig et al. Journal of Translational Medicine 2004, 2(44) (Year: 2004).*
Kita et al. (Leukemia Research 35 (2011) 787-792). (Year: 2011).*
Ott (Blood (2013) 122 (24): 3884-3891) (Year: 2013).*
American Chemical Society. Can Non-Hodgkin Lymphoma Be Prevented?https://www.cancer.org/cancer/types/non-hodgkin-lymphoma/causes-risks-prevention/prevention.html (Year: 2020).*
(J. Med. Oncl. Ther 2016; 1(2):62-71 (Year: 2016).*
Aoyama Y., et al., "Pharmacokinetics of Sepantronium Bromide (YM155), A Small-Molecule Suppressor of Survivin, in Japanese Patients with Advanced Solid Tumors: Dose Proportionality and Influence of Renal Impairment," Cancer Chemotherapy and Pharmacology, 2012, vol. 70(3), pp. 373-380.
Asahi, M. et al., "Survivin suppressant YM155 induces cell death via proteasomal degradation ofc-Myc in multiple myeloma cells," 15th International Myeloma Workshop, e237, Sep. 23-26, 1 page.
Extended European Search Report dated Jun. 27, 2022 for European Application No. 19849633.3, 7 pages.
Hidehiro, T. et al., "Low-level copy gain versus amplification of myc oncogenes in medulloblastoma: utility in predicting prognosis and survival. Laboratory investigation," J Neurosurg Pediatr, 3(1):61-5 (2009). doi: 10.3171/2008.10.PEDS08105, 1 page—Abstract.
International Search Report and Written Opinion for International Application No. PCT/US2021/050657 dated Dec. 13, 2021, 13 pages.
Maiello, M.R., et al., "EGFR and MEK Blockade in Triple Negative Breast Cancer Cells," Journal of Cellular Biochemistry, Dec. 2015, vol. 116(12), pp. 2778-2785.
Masuishi, T., et al., "Current Progress and Feasibility of Using Molecular-Targeted Agent Combinations for Metastatic Colorectal Cancer," Japanese Journal of Cancer and Chemotherapy, Apr. 2016, vol. 43(4), pp. 408-412.
Ohshima, K. et al., "Integrated analysis of gene expression and copy number identified potential cancer driver genes with amplification

(56) References Cited

OTHER PUBLICATIONS dependent overexpression in 1,454 solid tumors," Scientific Reports, 7:641 (2017), 13 pages; doi:0.1038/s41598-017-00219-3.

Tao Y., et al., "Survivin Selective Inhibitor YM155 Induce Apoptosis in SK-NEP-1 Wilms Tumor Cells," BMC Cancer, 2012, vol. 12, pp. 1-13.

Voges, Y. et al., "Effects of YM155 on survivin levels and viability in neuroblastoma cells with acquired drug resistance," Cell Death and Disease, 6:e2410 (2016), 11 pages; doi.10.2038/cddis.2016.257.

Radic-Sarikas, B. et al., "Lapatinib potentiates cytotoxicity of YM155 in neuroblastoma via inhibition of the ABCB1 efflux transporter," Scientific Reports, 7:3091 (2017), 8 pages; doi: 10.1038/s41598-017-03129-6.

Bridge, R. S. et al., "Molecular diagnosis of Ewing sarcoma/primitive neuroectodermal tumor in routinely processed tissue: a comparison of two FISH strategies and RT-PCR in malignant round cell tumors," Modern Pathology, 19:1-8, 2006.

Danielpour, D., et al., "Early Cellular Responses of Prostate Carcinoma Cells to Sepantronium Bromide (YM155) Involve Suppression of mTORC1 by AMPK," Scientific Reports, Aug. 8, 2019, vol. 9 pp. 1-17.

Dioufa, N. et al., "Survivin is a therapeutic target in Ewing sarcoma," The FASEB Journal, Apr. 1, 2015, No. 1, vol. 29 abstract.

Dos-Santos, K. C., et al., "Abstract B31: Cell-based screening of novel anticancer molecules for prostate cancer," Cancer Research. Dec. 31, 2013(Dec. 31, 2013) No. 19 Suppl. vol. 73, 1 page.

Ewing, J., "Diffuse Endothelioma of Bone," Proceedings of the New York Pathological Society. 1921; 21:17; 3 pages.

Freeman, W. M. et al., "Quantitative RT-PCR: Pitfalls and Potential," Bio Techniques, 26:112-125, 1999.

Greve, B. et al., "Survivin, a target to modulate the radiosensitivity of Ewing's sarcoma," Radiation therapy and oncology: organ of the German Roentgen Society, Oct. 10, 2012, vol. 188(11), pp. 1038-1047.

Hingorani, P. et al., "Survivin expression in Ewing sarcoma family of tumors," Journal of Clinical Oncology, May 20, 2012, vol. 29(15). Abstract. 1 page.

Hyman, D. M. et al., "Vemurafenib in Multiple Nonmelanoma Cancers with Braf V600 Mutations," N. Engl. J. Med., 373:726-736 (2015).

International Search Report and Written Opinion for Application No. PCT/CN2021/133165, mailed on Aug. 23, 2022, 16 pages.

International Search Report and Written Opinion for International Application No. PCT/CN2022/071439, mailed Oct. 10, 2022, 15 pages.

International Search Report and Written Opinion for International Application No. PCT/CN2023/071763, dated Apr. 27, 2023, 13 pages.

International Search Report and Written Opinion for International Application No. PCT/US2022/076460, mailed Dec. 15, 2022, 15 pages.

International Search Report and Written Opinion for International Application No. PCT/US2022/079938 dated Mar. 31, 2023, 19 pages.

International Search Report and Written Opinion for International Application No. PCT/CN2021/118866, mailed Jun. 15, 2022, 12 pages.

International Search Report and Written Opinion mailed Aug. 19, 2019 for International Application No. PCT/CN2018/115826, 9 pages.

Invitation to Pay Additional Fees for International Application PCT/US2022/079938, mailed Feb. 3, 2023, 3 pages.

Ito et al., "A Small-Molecule Suppressant of Survivin YM155 Induces Cell Death via Proteasomal Degradation of c-Myc in Multiple Myeloma Cells" Blood, vol. 126, Issue 23, Dec. 3, 2015, 2 pages.

Iwamoto, Y., "Diagnosis and Treatment of Ewing's Sarcoma," Jpn J Clin Oncol 2007; 37(2)79-89; doi:10.1093/jco/hyl142.

Kita, A. et al., "Antitumor effects of YM155, a novel survivin suppressant, against human aggressive non-Hodgkin lymphoma," Leukemia Research, 35(6):787-792 (2011).

McCuiston, A. et al., "Usefulness of NKX2.2 Immunohistochemistry for Distinguishing Ewing Sarcoma from Other Sinonasal Small Round Blue Cell Tumors, " Head and Neck Pathol, 12:89-94, 2018.

Nakahara, T. et al., "Broad spectrum and potent antitumor activities of YM155, a novel small-molecule survivin suppressant, in a wide variety of human cancer cell lines and xenograft models," Cancer Sci, 102, 3, 614-621, 2011.

Nyquist, M. D., et al., "Exploiting AR-Regulated Dmg Transport to Induce Sensitivity to the Survivin Inhibitor YM155," Molecular Cancer Research, May 31, 2017(May 31, 2017), No. 5, vol. 15, pp. 521-531.

Riggi, N. et al., "Ewing's Sarcoma," N Engl J Med 2021; 384:154-64; doi: 10.1056/NEJMra2028910.

Rodriguez-Martin, C. et al., "Molecular Approaches to Diagnosis in Ewing Sarcoma: RT-PCR," Methods Mol Biol. 2021; 2226:85-103. doi: 10.1007/978-1-0716-1020-6_7.

Selezneva, A.I. et al. "Complex Approach to Study Pharmacological Agents In Vitro, Ex Vivo, In Vivo," International Scientific Research Journal, 2015.—N. 6 (37) Part 2.—S. 125-127, 3 pages. Abstract.

Tolcher, A. W., et al., " A phase n study of YM155, a novel small-molecule suppressor of survivin, in castration-resistant taxane-pretreated prostate cancer," Annals of Oncology, Aug. 22, 2011, vol. 23, No. 4, pp. 968-973.

Wagner, V. et al., "Preclinical efficacy of sepantronium bromide (YM155) in multiple myeloma is conferred by down regulation of Mcl-1," Oncotarget, 5(21): 10237-10250 (2014).

Yamauchi, T. et al., "Sepantronium bromide (YM155) induces disruption of the ILF3/p54(nrb) complex, which is required for survivin expression," Biochemical and biophysical research communications, Jul. 27, 2012, vol. 425(4), pp. 711-716.

Yang, Y. et al., "Application of fluorescence in-situ hybridization and reverse transcription-polymerase chain reaction in molecular diagnosis of Ewing's sarcoma and primitive neuroectodermal tumor," Jun. 30, 2006, vol. 35(6), pp. 328-332. Abstract.

International Search Report and Written Opinion mailed Mar. 8, 2018 for International Application No. PCT/CN2017/086911, 12 pages.

International Search Report and Written Opinion mailed Aug. 31, 2018 for International Application No. PCT/US2018/035641, 9 pages.

Extended European Search Report dated Jan. 22, 2021 for European Application No. 18810472.3, 7 pages.

International Search Report and Written Opinion mailed Nov. 12, 2020 for International Application No. PCT/CN2020/074515, 13 pages.

International Search Report and Written Opinion mailed Apr. 27, 2021 for International Application No. PCT/US2021/16861, 10 pages.

International Search Report and Written Opinion mailed Nov. 10, 2020 for International Application No. PCT/CN2020/074516, 13 pages.

International Search Report and Written Opinion mailed Apr. 22, 2021 for International Application No. PCT/2021/016863, 12 pages.

Aburjania, Z. et al., "The Role of Notch3 in Cancer," The Oncologist, 23:900-911 (2018).

Asahi, M. et al., "YM155 suppresses proliferation and survival of multiple myeloma cells via proteasomal degradation of c-Myc.," J Mec Oncl Ther, 1(2):62-71 (2016).

Ashworth, T. D. et al., "Deletion-based mechanisms of Notch1 activation in T-ALL: key roles for RAG recombinase and a conserved internal translational start site in Notch1," Blood, 116(25):5455-5464 (2010).

Beltran, H., "The N-myc Oncogene: Maximizing its Targets, Regulation, and Therapeutic Potential," Mol Cancer Res, 12(6):815-822 (2014).

Boskovski, M. T. et al., "The heterotaxy gene GALNT11 glycosylates Notch to orchestrate cilia type and laterality," Nature, 504:456-459 (2013), including Methods and Extended Data, 11 pages.

Bundgaard, H., "Design of Prodrugs," pp. 7-9; 21-24, Elsevier Science Publishers, Amsterdam, 1985, 10 pages.

(56) References Cited

OTHER PUBLICATIONS

CAS Registry No. 781661-94-7, Nov. 16, 2004, 3 pages.
Cheng, X. J. et al., "Survivin inhibitor YM155 suppresses gastric cancer xenograft growth in mice without affecting normal tissues," Oncotarget, 7(6):7096-7109 (2016).
Cheson, B. D. et al., "Abstract 8502. Safety and efficacy of YM155 in diffuse large B-cell lymphoma (DLBCL)," Journal of Clinical Oncology, No. 15, Suppl vol. 27 (2009), 2 pages.
Chico, L. K. et al., "Targeting protein kinases in central nervous system disorders," Nat Rev Drug Discov., 8(11):892-909 (2009).
Coiffier, B. & Sarkozy, C., "Diffuse large B-cell lymphoma: R-CHOP failure—what to do?" Hematology Am Soc Hematol Educ Program, (1):366-378 (2016).
Darzynkiewicz, Z. et al., "Flow Cytometry in Analysis of Cell Cycle and Apoptosis," Semin Hematol, 38:179-193 (2001).
Ellisen, L. W. et al., "TAN-1, the Human Homolog of the *Drosophila* Notch Gene, Is Broken by Chromosomal Translocations in T Lymphoblastic Neoplasms," Cell, 66:649-661 (1991).
Ferrarotto, R. et al., "Activating NOTCH1 Mutations Define a Distinct Subgroup of Patients With Adenoid Cystic Carcinoma Who Have Poor Prognosis, Propensity to Bone and Liver Metastasis, and Potential Responsiveness to Notch1 Inhibitors," Journal of Clinical Oncology, 35(3):352-360 (2016).
Gall, J. G. & Pardue, M. L., "Formation and Detection of RNA-DNA Hybrid Molecules in Cytological Preparations," Proc Natl Acad Sci USA, 63(2):378-383 (1969).
Haydu, J. E. et al., "An activating intragenic deletion in NOTCH1 in human T-ALL," Blood, 119(22):5211-5214 (2012).
Kallioniemi, A. et al., "Comparative Genomic Hybridization for Molecular Cytogenetic Analysis of Solid Tumors," Science, 258:818-821 (1992).
Kawazu, M. et al., "Integrative analysis of genomic alterations in triple-negative breast cancer in association with homologous recombination deficiency," PLoS Genet, 13(6):e1006853 (2017), 23 pages; https://doi.org/10.1371/journal.pgen.1006853.
Liu, Z. et al., "Prognostic and biological significance of survivin expression in patients with diffuse large B-cell lymphoma treated with rituximab-CHOP therapy," Mod Pathol, (10):1297-314 (2015); doi:10.1038/modpathol.2015.94.
Luke, J. J. et al., "The Biology and Clinical Development of MEK Inhibitors for Cancer," Drugs, 74:2111-2128 (2014).
Minematsu, T. et al., "Carrier-Mediated Uptake of 1-(2-Methoxyethyl)-2-methyl-4,9-dioxo-3-(pyrazin-2-ylmethyl)-4,9-dihydro-1H-naphtho[2,3-d]imidazolium Bromide (YM155 Monobromide), a Novel Small-Molecule Survivin Suppressant, into Human Solid Tumor and Lymphoma Cells," Drug Metabolism and Disposition, 37(3):619-628 (2009).
Na, Y-S. et al., "YM155 Induces EGFR Suppression in Pancreatic Cancer," PLoS One, 7(6):e38625 (2012), 10 pages; doi:10.1371/journal.pone/0038625.
Nakahara, T. et al., "YM155, a Novel Small-Molecule Survivin Suppressant, Induces Regression of Established Human Hormone-Refractory Prostate Tumor Xenografts," Cancer Res, 67(17):8014-8021 (2007).
O'Neil, J et al., "FBW7 mutations in leukemic cells mediate NOTCH pathway activation and resistance to γ-secretase inhibitors," JEM, 204(8):1813-1824 (2007).
Parra, I. & Windle, B., "High resolution visual mapping of stretched DNA by fluorescent hybridization," Nature Genetics, 5:17-21 (1993).
Pinkel, D. & Albertson, D. G., "Comparative Genomic Hybridization," Annu. Rev. Genomics Hum. Genet., 6:331-354 (2005).
Puentes, X. S. et al., "Non-coding recurrent mutations in chronic lymphocytic leukaemia," Nature, 526:519-524 (2015), including Methods, 5 pages.
Rosati, E. et al., "NOTCH1 Aberrations in Chronic Lymphocytic Leukemia," Front. Oncol., 8:229 (2018), 20 pages; doi:10.3389/fonc.2018.00229.
Schouten, J. P. et al., "Relative quantification of 40 nucleic acid sequences by multiplex ligation-dependent probe amplification," Nucleic Acids Research, 30(12):e57 (2002), 13 pages.
Sulis, M. L. et al., "NOTCH1 extracellular juxtamembrane expansion mutations in T-ALL," Blood, 112:733-740 (2008).
Thomas, A. et al., "Refining the treatment of NSCLC according to histological and molecular subtypes," Nature Reviews Clinical Oncology, 12:511-526 (2015).
Thompson, B. J. et al., "The $SCF^{FBW7}$ ubiquitin ligase complex as a tumor suppressor in T cell leukemia," JEM, 204(8):1825-1835 (2007).
UniProtKB No. P46531, Apr. 7, 2021, 22 pages.
Van Agthoven, M. et al., "A review of recruitment criteria, patient characteristics and results of CHOP chemotherapy in prospective randomized phase III clinical trials for aggressive non-Hodgkin's lymphoma," The Hematology Journal, 4:399-409 (2003).
Wang, K. et al., "PEST Domain Mutations in Notch Receptors Comprise an Oncogenic Driver Segment in Triple-Negative Breast Cancer Sensitive to a γ-Secretase Inhibitor," Clin Cancer Res, 21(6):1487-1496 (2015).
Weng, A. P. et al., "Activating Mutations of NOTCH1 in Human T Cell Acute Lymphoblastic Leukemia," Science, 306:269-271 (2004).
Westhoff, B. et al., "Alterations of the Notch pathway in lung cancer," PNAS, 106(52):22293-22298 (2009).
Woo, S. M. et al., "YM155 enhances ABT-737-mediated apoptosis through Mcl-1 downregulation in Mcl-1-overexpressed cancer cells," Mol Cell Biochem, 429:91-102 (2017).
Ye, B. H. et al., "Alterations of a Zinc Finger-Encoding Gene, BCL-6, in Diffuse Large-Cell Lymphoma," Science, 262:747-750 (1993).
Zhao, M. et al., "Computational tools for copy number variation (CNV) detection using next-generation sequencing data: features and perspectives," BMC Bioinformatics, 14(Suppl 11):S1 (2013), 16 pages; http://www.biomedcentral.com/1471-2105/14/S11/S1.
Zhao, X. et al., "Survivin Inhibition Is Critical for Bcl-2 Inhibitor-Induced Apoptosis in Hepatocellular Carcinoma Cells," PLoS One, 6(8): e21980 (2011), 9 pages; doi:10.1371/journal.pone.0021980.
Zhong, Y. et al., "NOTCH 1 is a poor prognostic factor for breast cancer and is associated with breast cancer stem cells," Oncotargets and Therapy, 9:6865-6871 (2016).
Zhou, J. et al., "CDK4/6 or MAPK blockade enhances efficacy of EGFR inhibition in oesophageal squamous cell carcinoma," Nature Communications, 8:13897 (2017), 12 pages; https://doi.org/10.1038/ncomms13897.
International Search Report and Written Opinion mailed Jun. 21, 2021 for International Application No. PCT/CN2020/117167, 14 pages.
Gautam, P. et al., "Identification of selective cytotoxic and synthetic lethal drug responses in triple negative breast cancer cells, " Molecular Cancer, 15:34 (2016), 16 pages; doi. 10.1186/s12943-016-0517-3.
Warrier, N. M. et al., "Emerging Importance of Survivin in Stem Cells and Cancer: the Development of New Cancer Therapeutics," Stem Cell Reviews and Reports, 16:828-852 (2020).
Yamanaka, K. et al., "YM155, a selective survivin suppressant, inhibits tumor spread and prolongs survival in a spontaneous metastatic model of human triple negative breast cancer," International Journal of Oncology, 39:569-575 (2011).
De Falco, G. et al., "Burkitt lymphoma beyond MYC translocation: N-MYC and DNA methyltransferases dysregulation," BMC Cancer, 15:668 (2015); doi: 10.1186/s12885-015-1661-7, 13 pages.
De Jonge, A. V. et al., "Diffuse large B-cell lymphoma with MYC gene rearrangements. Current perspective on treatment of diffuse large B-cell lymphoma with MYC gene rearrangements; case series and review of the literature," European Journal of Cancer, 55:140-146 (2016).
Gene: MYC (ENSG00000136997), Gene ID: 4609, MYC proto-oncogene, bHLH transcription factor, updated on Dec. 25, 2023, 2 pages.
Haberl, S. et al., "MYC rearranged B-cell neoplasms: impact of genetics on classification," Cancer Genetics, 2016, http://dx.doi.org/coi:10.1016/j.cancergen.2016.08.007. Accepted Manuscript, 20 pages.
Leucci, E. et al,. "MYC translocation-negative classical Burkitt lymphoma cases: an alternative pathogenetic mechanism involving

(56) References Cited

OTHER PUBLICATIONS miRNA deregulation," J Pathol, 216:440-450 (2008). Published online Jul. 14, 2008 in Wiley InterScience (www.interscience.wiley.com); doi: 10.1002/path.2410.

Misale et al., (2014). "Blockade of EGFR and MEK intercepts heterogeneous mechanisms of acquired resistance to anti-EGFR therapies in colorectal cancer," Science Translational Medicine, 6(224):224ra26-1, 10 pages.

Molina et al., (2008). "Non-small cell lung cancer: epidemiology, risk factors, treatment, and survivorship," Mayo Clin Proc., 83(5):584-594, 19 pages.

Mundo, L. et al., "Molecular switch from MYC to MYCN expression in MYC protein negative Burkitt lymphoma cases," Blood Cancer Journal, 9:91 (2019); https://doi.org/10.1038/s41408-019-0252-2, 10 pages.

Winter, G. E. et al., "The solute carrier SLC35F2 enables YM155-mediated DNA damage toxicity," Nat Chem Biol., 10(9):768-773 (2014). doi:10.1038/nchembio.1590.

Bemark, M. et al., "The c-MYC allele that is translocated into the IgH locus undergoes constitutive hypermutation in a Burkitt's lymphoma line," Oncogene, 2000, vol. 19(30), pp. 3404-3410.

Extended European Search Report for European Application No. EP20210750599 dated Jan. 30, 2024, 10 pages.

Extended European Search Report for European Application No. EP21750128.7, mailed on Jan. 15, 2024, 15 pages.

Friedman, L. M. et al., "Fundamentals of Clinical Trials," 5th Ed., Springer Int'l Publishing, 2015, 5 pages.

Hann S. R. et al., "Proteins encoded by the human c-myc oncogene: differential expression in neoplastic cells," Molecular and Cellular Biology, 1984, vol. 4(11), pp. 2486-2497.

Johnson-Farley Nadine, et al., "ABT-199, a BH3 mimetic that specifically targets Bcl-2, enhances the antitumor activity of chemotherapy, bortezomib and JQ1 in "double hit" lymphoma cells", Leukemia & Lymphoma, Informa Healthcare, UK, vol. 56, No. 7, Jun. 30, 2015 (Jun. 30, 2015), pp. 2146-2152.

Li W. et al., "Targeting MYC activity in double-hit lymphoma with MYC and BCL2 and/or BCL6 rearrangements with epigenetic bromodomain inhibitors", Journal of Hematology & Oncology, vol. 12, No. 1, Jul. 9, 2019 (Jul. 9, 2019), pp. 1-13.

Llombart-Bosch, A. et al., "Histological heterogeneity of Ewing's sarcoma/PNET: an immunohistochemical analysis of 415 genetically confirmed cases with clinical support," Virchows Arch., 455:397-411 (2009).

Matasar M. J. et al., "Overview of Lymphoma Diagnosis and Management," Radiologic Clinics of North America, 2008, vol. 46(2), pp. 175-198.

Rickman David, S. et al., "The Expanding World of N-MYC-Driven Tumors", Cancer Discovery, 8(2), Feb. 1, 2018, pp. 150-163.

Sand, L. G. L. et al., "CXCL14, CXCR7 expression and CXCR4 splice variant ratio associate with survival and metastases in Ewing sarcoma patients," Eur. J. Cancer, 51:2624-2633 (2015).

Satoh, T. et al., "Phase I Study of YM155, a Novel Survivin Suppressant, in Patients with Advanced Solid Tumors," Clin. Canc. Res., 15:3872-3880 (2009).

Yamanaka, K. et al., "Antitumor Activity of YM155, a Selective Small-Molecule Survivin Suppressant, Alone and in Combination with Docetaxel in Human Malignant Melanoma Models", Clinical Cancer Research, vol. 17, No. 16, Aug. 14, 2011, pp. 5423-5431.

Nguyen L. et al.: "The Role of c-MYC in B-Cell Lymphomas: Diagnostic and Molecular Aspects", Genes, 2017, vol. 8, article 116, 23 pages.

Zhao N., et al., "YM155, a Survivin Suppressant, Triggers PARP-dependent Cell Death (Parthanatos) and Inhibits Esophageal Squamous-cell Carcinoma Xenografts in Mice", Oncotarget, vol. 6, No. 21, Jun. 15, 2015 (Jun. 15, 2015), pp. 18448-18459.

\* cited by examiner

BIOMARKERS FOR CANCER THERAPY

CROSS-REFERENCE TO RELATED APPLICATIONS

This application is a U.S. National Phase application filed under 35 U.S.C. § 371(c) of International Application No. PCT/US2019/046124, filed Aug. 12, 2019, which claims priority to and the benefit of PCT/CN2018/100206, filed Aug. 13, 2018; and PCT/CN2018/115826, filed Nov. 16, 2018, each of which is incorporated by reference in its entirety.

BACKGROUND

Technical Field

Embodiments of the present disclosure relate to the use of a MYC gene as a biomarker for predicting therapeutic efficacy of survivin inhibitors such as YM155 monobromide in cancer therapy, and related kits, compositions, and methods for diagnosing and treating cancer in a subject in need thereof.

Description of the Related Art

YM155 monobromide is a small-molecule survivin inhibitor that induces the down-regulation of survivin and exhibits potent antitumor activity (see, e.g., Minematsu et al., Drug Metabolism and Disposition, 37:619-628, 2008). YM-155 exerts anti-tumor effects in various in vivo cancer models, including prostate, pancreatic, and lung cancer (see, e.g., Nakahara et al., Cancer Research 67:8014-8021, 2007; and Na et al., PLoS One 7(6), 2012).

However, there is a need in the art to better predict the anti-cancer therapeutic efficacy of YM155 monobromide, and thereby identify patients that will benefit most from treatment with this chemotherapeutic, and others.

BRIEF SUMMARY

Embodiments of the present disclosure include methods for treating cancer in a subject in need thereof, comprising:
(a) determining MYC gene copy number, or MYC gene chromosomal location site, in a sample of cancer tissue from the subject; and
(b) administering YM155 monobromide [1-(2-Methoxyethyl)-2-methyl-4,9-dioxo-3-(pyrazin-2-ylmethyl)-4,9-dihydro-1H-naphtho[2,3-d]imidazolium bromide], or an analog or derivative thereof, to the subject if MYC gene copy number in the cancer tissue is increased relative to that of a MYC gene copy number reference, or if MYC gene chromosomal location site in the cancer tissue is translocated relative to that of a MYC gene chromosomal location site reference,
thereby treating cancer in the subject in need thereof.

Some embodiments include administering to the subject a chemotherapeutic agent excluding (or other than) YM155 monobromide if MYC gene copy number in the cancer tissue is not substantially increased relative to that of the MYC gene copy number reference, or if MYC gene chromosomal location site in the cancer tissue is not translocated relative to that of the MYC gene chromosomal location site reference.

Also included are methods for predicting therapeutic response to YM155 monobromide [1-(2-Methoxyethyl)-2-methyl-4,9-dioxo-3-(pyrazin-2-ylmethyl)-4,9-dihydro-1H-naphtho[2,3-d]imidazolium bromide], or an analog or derivative thereof, in a subject with cancer, comprising
(a) determining MYC gene copy number, or MYC gene chromosomal location site, in a sample of cancer tissue from the subject; and
(b) (i) characterizing the subject as responsive to YM155 monobromide therapy if MYC gene copy number in the cancer tissue is increased relative to that of a MYC gene copy number reference, or if the MYC gene chromosomal location site in the cancer tissue is translocated relative to that of a MYC gene chromosomal location site reference; or
(ii) characterizing the subject as non-responsive to YM155 monobromide therapy if MYC gene copy number in the cancer tissue is not substantially increased relative to that of the MYC gene copy number reference, or if the MYC gene chromosomal location site in the cancer tissue is not translocated relative to that of the MYC gene chromosomal location site reference,
thereby predicting therapeutic response to YM155 monobromide in the subject with cancer.

Some embodiments include administering YM155 monobromide to the subject if the subject is characterized as responsive to YM155 monobromide therapy. Some embodiments include administering to the subject a chemotherapeutic agent excluding YM155 monobromide if the subject is characterized as non-responsive to YM155 monobromide therapy.

In some embodiments, the MYC gene copy number in the cancer tissue is increased by about or at least about 1.5, 2, 3, 4, 5, 6, 7, 8, 9, or 10-fold relative to that of the MYC gene copy number reference.

Some embodiments comprise determining MYC gene copy number in the cancer tissue by array comparative genome hybridization (aCGH), single nucleotide polymorphism (SNP) array, copy number variation (CNV) sequencing, or multiplex ligation-dependent probe amplification (MLPA). Some embodiments comprise determining MYC gene chromosomal location site in the cancer tissue by in situ hybridization (ISH), fluorescence in situ hybridization (FISH), next generation sequencing (NGS), or comparative genome hybridization (CGH). Some embodiments comprise obtaining the MYC gene copy number reference from a database, or determining the MYC gene copy number reference from a non-cancerous tissue from a control, optionally by aCGH, SNP array, CNV sequence, or MLPA. Some embodiments comprise obtaining the MYC gene chromosomal location site reference from a database, or determining the MYC gene chromosomal location site reference from a non-cancerous tissue from a control, optionally by ISH, FISH, NGS, or CGH.

Some embodiments comprise obtaining the sample of cancer tissue from the subject. In certain embodiments, the sample of cancer tissue is a surgical sample, a biopsy sample, a pleural effusion sample, or an ascetic fluid sample obtained from the subject, optionally selected from one or more of lung, blood, breast, gastrointestinal (stomach, colon, rectal), ovarian, pancreatic, liver, bladder, cervical, neuronal, uterine, salivary gland, kidney, prostate, thyroid, or muscle tissue.

In certain embodiments, the subject is a human subject.
In certain embodiments, the cancer is selected from one or more of carcinoma, sarcoma such as rhabdomyosarcoma, for example, alveolar rhabdomyosarcoma (including sarcoma originating in the bones, tendons, cartilage, muscle, fat, fibrous, blood vessels, adipose, and/or connective tissue), neuroblastoma, medulloblastoma, astrocytoma, glioblastoma multiforme, retinoblastoma, myeloma, leukemia, lymphoma (including Hodgkin's lymphoma and Non-Hodgkin's lymphoma), adenosquamous carcinoma, carcinosarcoma, mixed mesodermal tumor, teratocarcinoma, lung cancer (including non-small cell lung cancer, small cell lung cancer, adenocarcinoma, and squamous carcinoma of the lung), breast cancer (including metastatic breast cancer), gastrointestinal cancer, stomach cancer, colorectal cancer, colon cancer, rectal cancer, ovarian cancer, pancreatic cancer, liver cancer, bladder cancer, cervical cancer, glioblastoma, uterine carcinoma, salivary gland carcinoma, kidney or renal cancer (e.g., Wilm's tumor), prostate cancer, thyroid cancer, and head and neck cancer.

In certain embodiments, the MYC gene is selected from MYCC and MYCN. In specific embodiments, the MYC gene is MYCC and the cancer is selected from lung cancers and blood cancers, optionally leukemias and lymphomas. In specific embodiments, the MYC gene is MYCN and the cancer is selected from neuroblastoma, small cell lung cancer, prostate cancer, alveolar rhabdomyosarcoma, medulloblastoma, glioblastoma multiforme, retinoblastoma, and breast cancer.

Also included is the use of a diagnostic kit for determining therapeutic response to YM155 monobromide [1-(2-Methoxyethyl)-2-methyl-4,9-dioxo-3-(pyrazin-2-ylmethyl)-4,9-dihydro-1H-naphtho[2,3-d]imidazolium bromide], or an analog or derivative thereof, therapy in a subject with cancer, comprising means for measuring MYC gene copy number, or MYC gene chromosomal location site, in a sample of tissue from the subject, including cancer tissue and non-cancerous tissue.

In certain embodiments, the means for measuring MYC gene copy number comprise reagents for performing a diagnostic assay selected from one or more of array comparative genome hybridization (aCGH), single nucleotide polymorphism (SNP) array, copy number variation (CNV) sequencing, and multiplex ligation-dependent probe amplification (MLPA) on a human MYC gene.

In certain embodiments, the means for measuring MYC gene chromosomal location site comprise reagents for performing a diagnostic assay selected from one or more of in situ hybridization (ISH), fluorescence in situ hybridization (FISH), next generation sequencing (NGS), and comparative genome hybridization (CGH) on a human MYC gene. Some embodiments comprise a MYC gene copy number reference value obtained from a database, or determined from a non-cancerous tissue from a control. Some embodiments comprise a MYC gene chromosomal location site reference obtained from a database, or determined from a non-cancerous tissue from a control.

Also included are patient care kits, comprising:
(a) means for measuring MYC gene copy number, or MYC gene chromosomal location site, in a sample of tissue from a subject, including cancer tissue and non-cancerous tissue; and
(b) YM155 monobromide [1-(2-Methoxyethyl)-2-methyl-4,9-dioxo-3-(pyrazin-2-ylmethyl)-4,9-dihydro-1H-naphtho[2,3-d]imidazolium bromide], or an analog or derivative thereof.

In certain embodiments, the means for measuring MYC gene copy number comprise reagents for performing a diagnostic assay selected from one or more of array comparative genome hybridization (aCGH), single nucleotide polymorphism (SNP) array, copy number variation (CNV) sequencing, and multiplex ligation-dependent probe amplification (MLPA) on a human MYC gene. In certain embodiments, the means for measuring MYC gene chromosomal location site comprise reagents for performing a diagnostic assay selected from one or more of in situ hybridization (ISH), fluorescence in situ hybridization (FISH), next generation sequencing (NGS), and comparative genome hybridization (CGH) on a human MYC gene.

Some embodiments comprise a MYC gene copy number reference value obtained from a database, or determined from a non-cancerous tissue from a control. Some embodiments comprise a MYC gene chromosomal location site reference obtained from a database, or determined from a non-cancerous tissue from a control.

In some uses or kits, the cancer is selected from one or more of carcinoma, sarcoma such as rhabdomyosarcoma, for example, alveolar rhabdomyosarcoma, (including sarcoma originating in the bones, tendons, cartilage, muscle, fat, fibrous, blood vessels, adipose, and/or connective tissue), neuroblastoma, medulloblastoma, astrocytoma, glioblastoma multiforme, retinoblastoma, myeloma, leukemia, lymphoma (including Hodgkin's lymphoma and Non-Hodgkin's lymphoma), adenosquamous carcinoma, carcinosarcoma, mixed mesodermal tumor, teratocarcinoma), lung cancer (including non-small cell lung cancer, small cell lung cancer, adenocarcinoma, and squamous carcinoma of the lung), breast cancer (including metastatic breast cancer), gastrointestinal cancer, stomach cancer, colorectal cancer, colon cancer, rectal cancer, ovarian cancer, pancreatic cancer, liver cancer, bladder cancer, cervical cancer, glioblastoma, uterine carcinoma, salivary gland carcinoma, kidney or renal cancer (e.g., Wilm's tumor), prostate cancer, thyroid cancer, and head and neck cancer.

In some uses or kits, the MYC gene is selected from MYCC and MYCN. In specific instances, the MYC gene is MYCC and the cancer is selected from lung cancers and blood cancers, optionally leukemias and lymphomas. In particular instances, the MYC gene is MYCN and the cancer is selected from neuroblastoma, small cell lung cancer, prostate cancer, alveolar rhabdomyosarcoma, medulloblastoma, glioblastoma multiforme, retinoblastoma, and breast cancer.

BRIEF DESCRIPTION OF THE DRAWINGS

FIG. 9A shows the tumor growth curve, and FIG. 9B presents the data as the means±SD of tumor volume (n=5). **p<0.01 compared with the vehicle group.

FIG. 10A shows the tumor growth curve, and FIG. 10B presents the data as the means±SD of tumor volume (n=8).

FIG. 11A shows the tumor growth curve, and FIG. 11B presents the data as the means±SD of tumor volume (n=3). **p<0.01 compared with the vehicle group.

FIG. 12A shows the tumor growth curve, and FIG. 12B presents the data as the means±SD of tumor volume (n=3).

FIG. 13A shows the tumor growth curve, and FIG. 13B presents the data as the means±SD of tumor volume (n=3).

FIG. 14A shows the tumor growth curve, and FIG. 14B presents the data as the means±SD of tumor volume (n=2 in vehicle; n=3 in YM155-treated).

DETAILED DESCRIPTION

Figure 1:
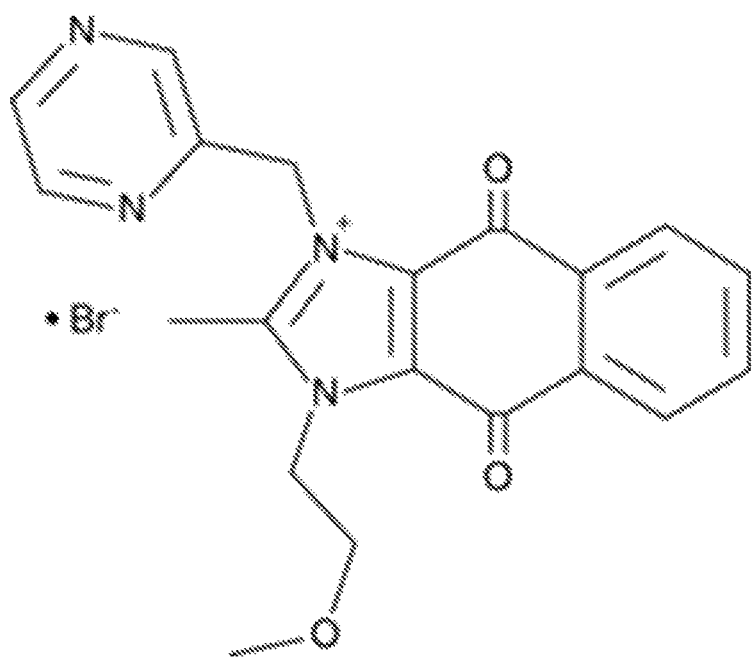
FIG. 1 shows the chemical structure of YM155 monobromide (CAS 781661-94-7).

Embodiments of the present disclosure relate to the surprising discovery that amplification and/or translocation of the MYC gene in human malignancies associate with increased anti-cancer efficacy of survivin inhibitors, such as YM155 monobromide, and can therefore be used as biomarker(s) to optimize cancer therapy by those agents and others. Without wishing to be bound by any one theory, it is believed that MYC oncogene expression in MYC-amplified or MYC-translocated cancer cells is otherwise pro-apoptotic, except that its pro-apoptotic signaling is negatively-regulated by survivin, a member of the inhibitor of apoptosis (IAP) protein family that inhibits caspases and blocks cell death. Thus, it is expected that survivin inhibitors such as YM155 monobromide can be used to block the apoptosis-inhibiting activity of survivin in the context of MYC amplification and/or translocation, favor the pro-apoptotic signaling of MYC to increase cancer cell death, and thereby provide optimal therapeutic efficacy in this context.

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

For the purposes of the present disclosure, the following terms are defined below.

The articles "a" and "an" are used herein to refer to one or to more than one (i.e., to at least one) of the grammatical object of the article. By way of example, "an element" means one element or more than one element.

An "antagonist" or "inhibitor" refers to biological structure or chemical agent that interferes with or otherwise reduces the physiological action of another molecule, such as a protein (e.g., survivin). In some instances, the antagonist or inhibitor specifically binds to the other molecule and/or a functional ligand of the other molecule. In some instances, the antagonist or inhibitor down-regulates the expression of the other molecule (e.g., survivin). Included are full and partial antagonists.

An "agonist" or "activator" refers to biological structure or chemical agent that increases or enhances the physiological action of another agent or molecule. In some instances, the agonist specifically binds to the other agent or molecule. Included are full and partial agonists.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The "half maximal inhibitory concentration" (or "$IC_{50}$") is a measure of the potency of an agent in inhibiting a specific biological or biochemical function. This quantitative measure indicates how much of a particular agent (inhibitor) is needed to inhibit a given biological process (or component of a process, i.e. an enzyme, cell, cell receptor or microorganism) by half. The values are typically expressed as molar concentration. The concentration is commonly used as a measure of antagonist drug potency in pharmacological research. In some instances, $IC_{50}$ represents the concentration of an agent that is required for 50% inhibition in vitro. The $IC_{50}$ of an agent can be determined by constructing a dose-response curve and examining the effect of different concentrations of the agent on the desired activity, for example, inhibition of tumor cell proliferation, tumor-cell killing.

An "increased" or "enhanced" amount is typically a "statistically significant" amount, and may include an increase that is about or at least about 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 50, 60, 70, 80, 90, 100, 200, 300, 400, 500, or 1000 fold, or about or at least about 5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000%, relative to that of a reference or control (including all integers and ranges in between). A "decreased" or "reduced" amount is typically a "statistically significant" amount, and may include a decrease that is about or at least about 1.2, 1.4, 1.6, 1.8, 2, 3, 4, 5, 6, 7, 8, 9, 10, 15, 20, 30, 50, 60, 70, 80, 90, 100, 200, 300, 400, 500, 1000 fold, or about or at least about 5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000%, relative to that of a reference or control (including all integers and ranges in between).

The term "polynucleotide" and "nucleic acid" includes mRNA, RNA, cRNA, cDNA, and DNA including genomic DNA. The term typically refers to polymeric form of nucleotides of at least 10 bases in length, either ribonucleotides or deoxynucleotides or a modified form of either type of nucleotide. The term includes single and double stranded forms of DNA.

A "gene" refers to a hereditary unit consisting of a sequence of DNA that occupies a specific location on a chromosome and codes for a functional molecule or protein. The structure of a gene consists of many elements of which the actual protein coding sequence is often only a small part. These elements include DNA regions that are not transcribed as well as untranslated regions of the RNA. Additionally, genes can have expression-altering regulatory regions that lie many kilobases upstream or downstream of the coding sequence. The information in a gene can also be represented by (or found in) a sequence of RNA or encoded protein.

A "subject" or a "subject in need thereof" includes a mammalian subject such as a human subject.

By "statistically significant" it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" means nearly totally or completely, for instance, 95% or greater of some given quantity.

"Therapeutic response" refers to improvement of symptoms (whether or not sustained) based on the administration of the therapeutic response.

As used herein, the terms "therapeutically effective amount", "therapeutic dose," "prophylactically effective amount," or "diagnostically effective amount" is the amount of an agent needed to elicit the desired biological response following administration.

As used herein, "treatment" of a subject (e.g. a mammal, such as a human) or a cell is any type of intervention used in an attempt to alter the natural course of the subject or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied to every other embodiment unless expressly stated otherwise.

The present disclosure relates, in part, to the surprising discovery that amplifications and/or translocations of the MYC gene in human malignancies associate with increased anti-cancer efficacy of the chemotherapeutic agent YM155 monobromide, and can thus be used as biomarkers to optimize cancer therapy by that agent and others.

Embodiments of the present disclosure therefore include methods for treating cancer in a subject in need thereof, comprising (a) determining MYC gene copy number, or MYC gene chromosomal location site, in a sample of cancer tissue from the subject; and (b) administering YM155 monobromide [1-(2-Methoxyethyl)-2-methyl-4,9-dioxo-3-(pyrazin-2-ylmethyl)-4,9-dihydro-1H-naphtho[2,3-d]imidazolium bromide] to the subject if MYC gene copy number in the cancer tissue is increased relative to that of a MYC gene copy number reference, or if MYC gene chromosomal location site in the cancer tissue is translocated relative to that of a MYC gene chromosomal location site reference, thereby treating cancer in the subject in need thereof. Certain embodiments include administering to the subject a chemotherapeutic agent excluding (or other than) YM155 monobromide if MYC gene copy number in the cancer tissue is not substantially increased (e.g., the same or less than about 1.1 fold increase) relative to that of the MYC gene copy number reference, or if MYC gene chromosomal location site in the cancer tissue is not translocated relative to that of the MYC gene chromosomal location site reference.

Also included are methods for predicting therapeutic response to YM155 monobromide [1-(2-Methoxyethyl)-2-methyl-4,9-dioxo-3-(pyrazin-2-ylmethyl)-4,9-dihydro-1H-naphtho[2,3-d]imidazolium bromide] in a subject with cancer, comprising (a) determining MYC gene copy number, or MYC gene chromosomal location site, in a sample of cancer tissue from the subject; and (b) (i) characterizing the subject as responsive to YM155 monobromide therapy if MYC gene copy number in the cancer tissue is increased relative to that of a MYC gene copy number reference, or if MYC gene chromosomal location site in the cancer tissue is translocated relative to that of a MYC gene chromosomal location site reference; or (ii) characterizing the subject as non-responsive to YM155 monobromide therapy if MYC gene copy number in the cancer tissue is not substantially increased (e.g., the same or less than about 1.1 fold increase) relative to that of the MYC gene copy number reference, or if MYC gene chromosomal location site in the cancer tissue is not translocated relative to that of the MYC gene chromosomal location site reference, thereby predicting therapeutic response to YM155 monobromide in the subject with cancer. Certain embodiments include administering YM155 monobromide to the subject if the subject is characterized as responsive to YM155 monobromide therapy. Some embodiments include administering to the subject a chemotherapeutic agent excluding (or other than) YM155 monobromide if the subject is characterized as non-responsive to YM155 monobromide therapy.

The "MYC gene" or "MYC oncogene" refers to a family of proto-oncogenes that encode transcription factors, examples of which include c-Myc (also MYCC) and N-myc (also MYCN).

The MYCC gene encodes a nuclear phosphoprotein that plays a role in cell cycle progression, apoptosis, and cellular transformation. The encoded protein forms a heterodimer with the related transcription factor MAX. This complex binds to the E box DNA consensus sequence and regulates the transcription of specific target genes. There is evidence to show that translation initiates both from an upstream, in-frame non-AUG (CUG) and a downstream AUG start site, resulting in the production of two isoforms with distinct N-termini. In the human genome, the MYCC gene is located on chromosome 8:127, 735, 434-127, 741, 434, forward strand (see, e.g., FIG. 5 and FIG. 6; and Gene: MYC ENSG00000136997).

The MYCN gene encodes a protein with a basic helix-loop-helix (bHLH) domain. It is located in the cell nucleus and dimerizes with another bHLH protein to bind DNA. MYCN is over-expressed in a number of different types of cancer, including, for example, neuroblastoma, rhabdomyosarcoma, medulloblastoma, astrocytoma, glioblastoma, retinoblastoma, prostate cancer, breast cancer, Wilms' tumour, and small cell lung cancer (see, for example, Beltran, Mol Cancer Res. 12:815-822, 2014). Indeed, MYCN amplification is an adverse prognostic factor in neuroblastoma. The amplicon (material co-amplified with MYCN) varies among subjects, and in certain instances includes, for example, the DDX1 gene. In some instances, MYCN amplification correlates with a 1p36 deletion and a gain of chromosome 17q. In the human genome, the MYCN gene is located on the the short (p) arm of chromosome 2 at position 24.3 (Cytogenetic Location at 2p24.3; Molecular Location at base pairs 15,940,438 to 15,947,007 on chromosome 2; see also FIG. 8).

Thus, in certain embodiments, the MYC gene is selected from MYCC and MYCN.

"YM155 monobromide" refers to the small molecule [1-(2-Methoxyethyl)-2-methyl-4,9-dioxo-3-(pyrazin-2-ylmethyl)-4,9-dihydro-1H- naphtho[2,3-d]imidazolium bromide], having the molecular formula $C_{20}H_{19}N_4O_3 \cdot Br$, and the CAS Number 781661-94-7, and includes pharmaceutically-acceptable salts and acids thereof. Also included are biologically-active or equivalent analogs and/or derivatives of YM155 monobromide.

As noted above, in some instances, the MYC gene copy number in the cancer tissue is increased relative to that of the MYC gene copy number reference. In particular embodiments, the MYC gene copy number in the cancer tissue is increased by a statistically significant amount relative to that of the MYC gene copy number reference. In some embodiments, the MYC gene copy number in the cancer tissue is increased by about or at least about 1.2, 1.3, 1.4, 1.5, 1.6, 1.7, 1.8, 1.9, 2, 2.5, 3, 3.5, 4, 4.5, 5, 6, 7, 8, 9, or 10-fold (or more) relative to that of the MYC gene copy number reference.

The MYC gene copy number in the cancer tissue can be determined by any variety of methods. For example, in some embodiments, the MYC gene copy number is determined by array comparative genome hybridization (aCGH), single nucleotide polymorphism (SNP) array, copy number variation (CNV) sequencing, or multiplex ligation-dependent probe amplification (MLPA). Certain embodiments thus include the step of determining or detecting copy number of a MYC gene in a sample of cancer tissue from a subject in need thereof. Also included is the step of comparing the copy number of a MYC gene in a sample of cancer tissue relative to that of a MYC gene copy number reference.

The MYC gene chromosomal location site in the cancer tissue can be determined by any variety of methods. For example, in some embodiments, the MYC gene chromosomal location site in the cancer tissue is determined by in situ hybridization (ISH), fluorescence in situ hybridization (FISH), next generation sequencing (NGS), or comparative genome hybridization (CGH). Certain embodiments thus include the step of determining or detecting the MYC gene chromosomal location site in a sample of cancer tissue from a subject in need thereof. Also included is the step of comparing the MYC gene chromosomal location site in the cancer tissue relative to that of a MYC gene chromosomal site reference.

CGH refers to a molecular cytogenetic method for analyzing copy number variations (CNVs) relative to ploidy level in the DNA of a test sample compared to a reference sample, without the need for culturing cells. This technique allows quick and efficient comparisons between two genomic DNA samples arising from two sources, which are most often closely related, because it is suspected that they contain differences in terms of either gains or losses of either whole chromosomes or subchromosomal regions (a portion of a whole chromosome). The technique was originally developed for the evaluation of the differences between the chromosomal complements of solid tumor and normal tissue (see, e.g., Kallioniemi et al., Science. 258 (5083): 818-821, 1992). The use of DNA microarrays in conjunction with CGH techniques has led to the development of a more specific form of array CGH (aCGH), allowing for a locus-by-locus measure of CNV with increased resolution as low as 100 kilobases (see, e.g., Pinkel, Annu Rev Genom Hum Genet. 6:331-354, 2005). CNV is a prevalent form of critical genetic variation that leads to an abnormal number of copies of large genomic regions in a cell, and high-resolution sequence data can be analyzed by next-generation sequencing (NGS) to identify the same (see, e.g., Zhao et al., BMC Bioinformatics. 14 Suppl 11:S1, 2013). MLPA refers to a variation of the multiplex polymerase chain reaction that permits amplification of multiple targets with only a single primer pair (see, e.g., Schouten et al., Nucleic Acids Res. 30 (12): e57, 2002). In situ hybridization (ISH) and fluorescent in situ hybridization (FISH) refer to a type of hybridization that uses a labeled complementary DNA, RNA or modified nucleic acids strand (i.e., probe) to localize a specific DNA or RNA sequence in a portion or section of tissue (in situ) (see, e.g., Parra & Windle, Nature Genetics. 5:17-21, 1993; and Gall & Pardue, PNAS USA. 63: 378-383, 1969). Thus, in some instances, the methods and kits described herein employ any one or more of the foregoing techniques and/or comprise reagents for performing the same.

Figure 5:
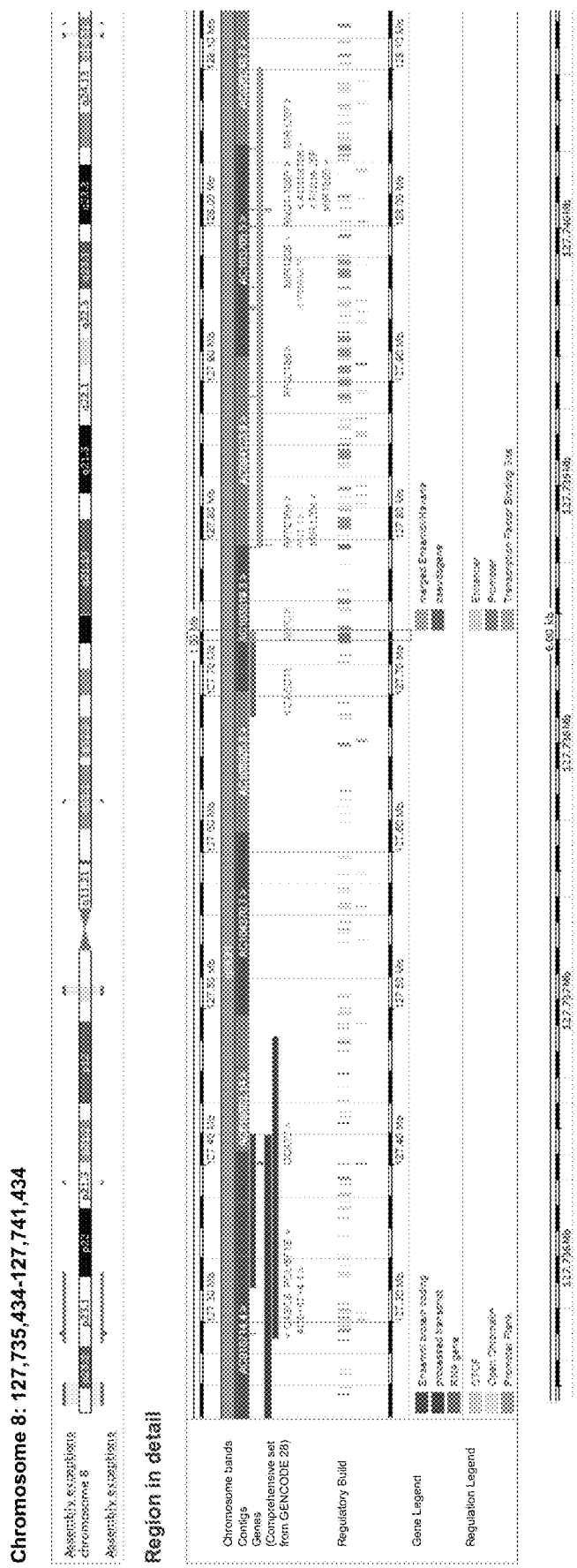
FIGS. 5 and 6 provide genomic information for the human MYC gene (see http://uswestensembl.org/Homo_sapiens/Location/View?db=core;g=ENSG00000136997; r=8: 127735 434-127742951).
Figure 6:
Figure 8:
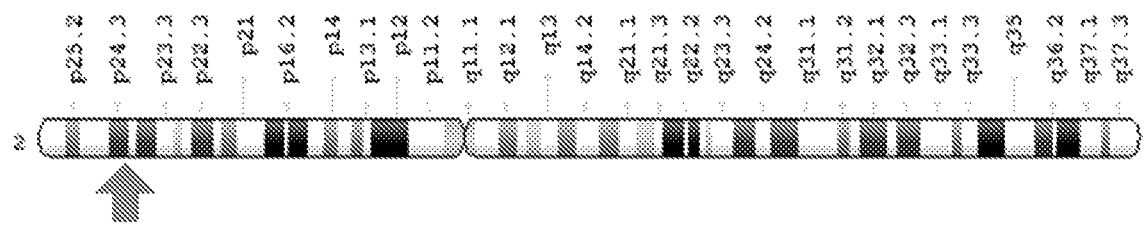
FIG. 8 shows the location of the MYCN gene on the short (p) arm of chromosome 2 at position 24.3.
Figure 9A:
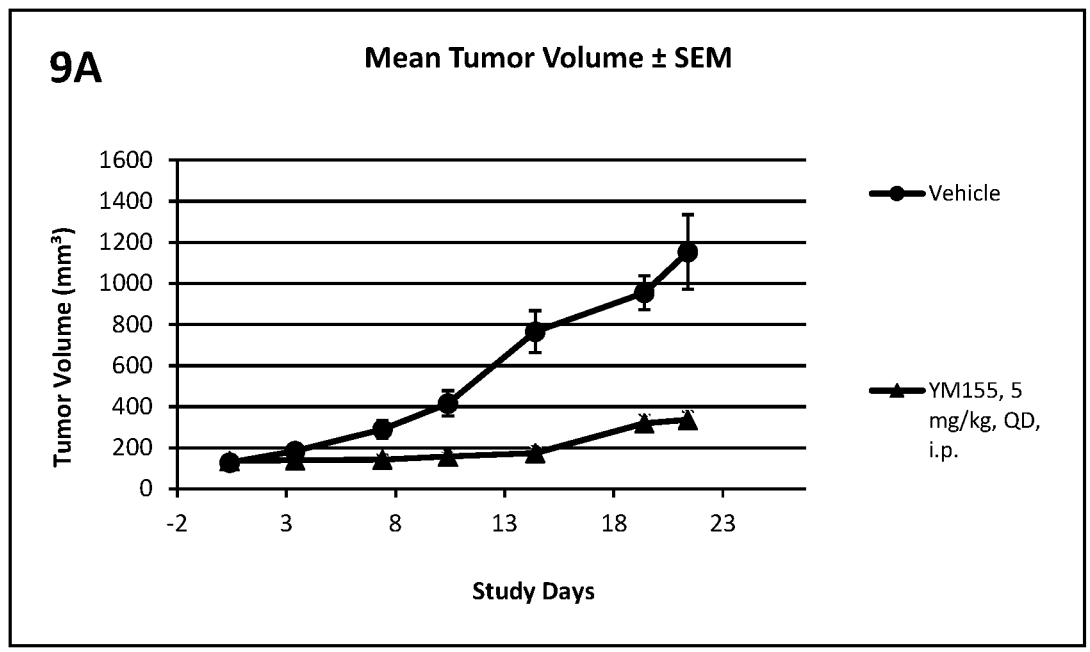
FIGS. 9A-9B show the antitumor effect of YM155 in HCC827 xenografts in mice.
Figure 9B:
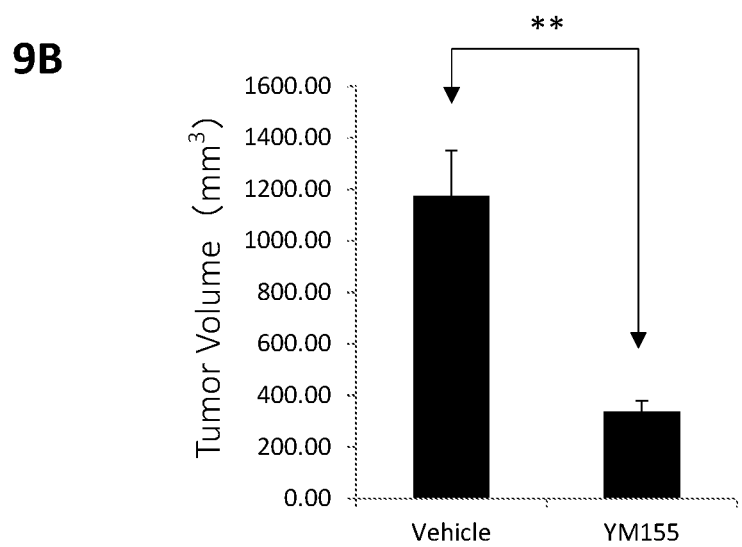
Figure 10A:
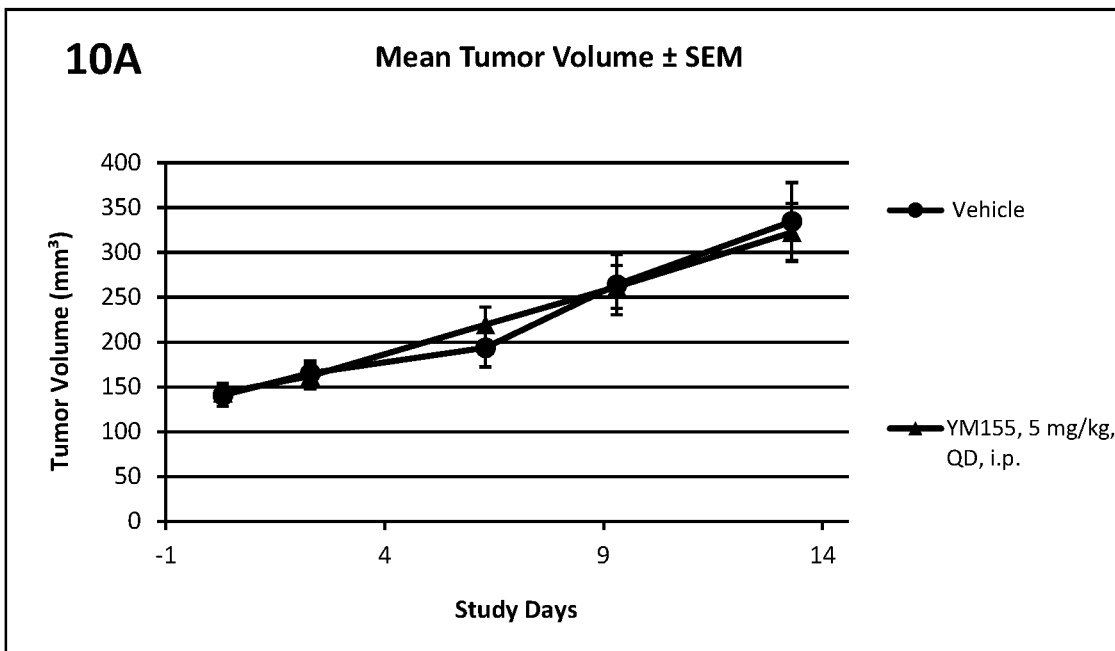
FIGS. 10A-10B show the antitumor effect of YM155 in HCC4006 xenografts in mice.
Figure 10B:
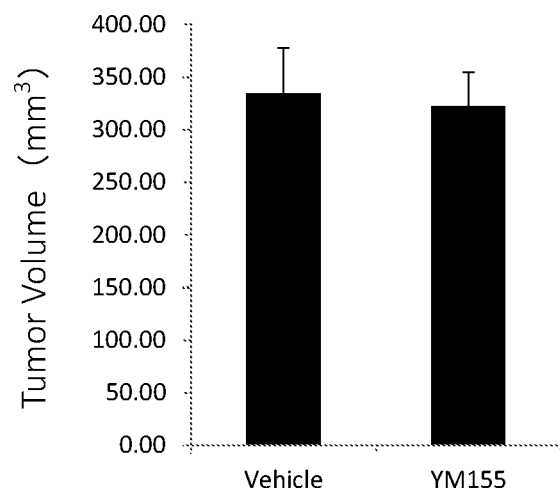
Figure 11A:
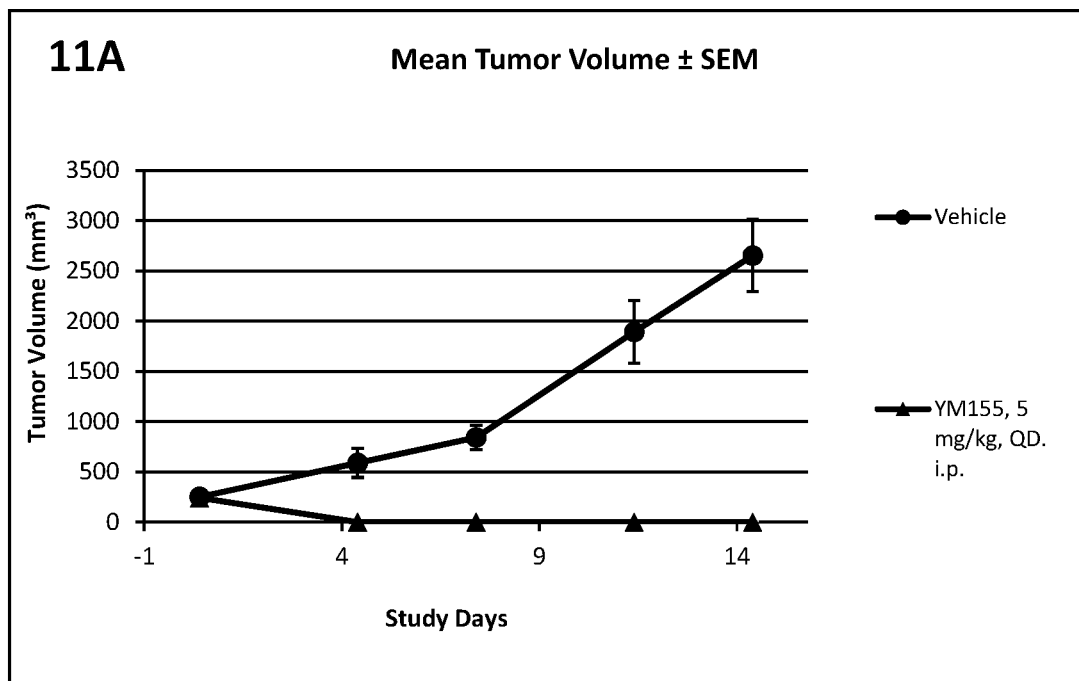
FIGS. 11A-11B show the antitumor effect of YM155 in RAMOS xenografts in mice.
Figure 11B:
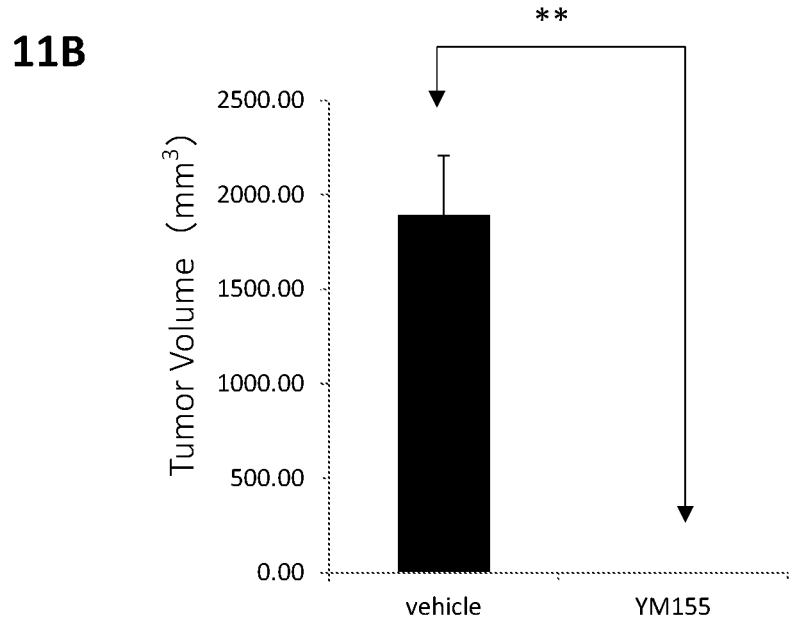
Figure 12A:
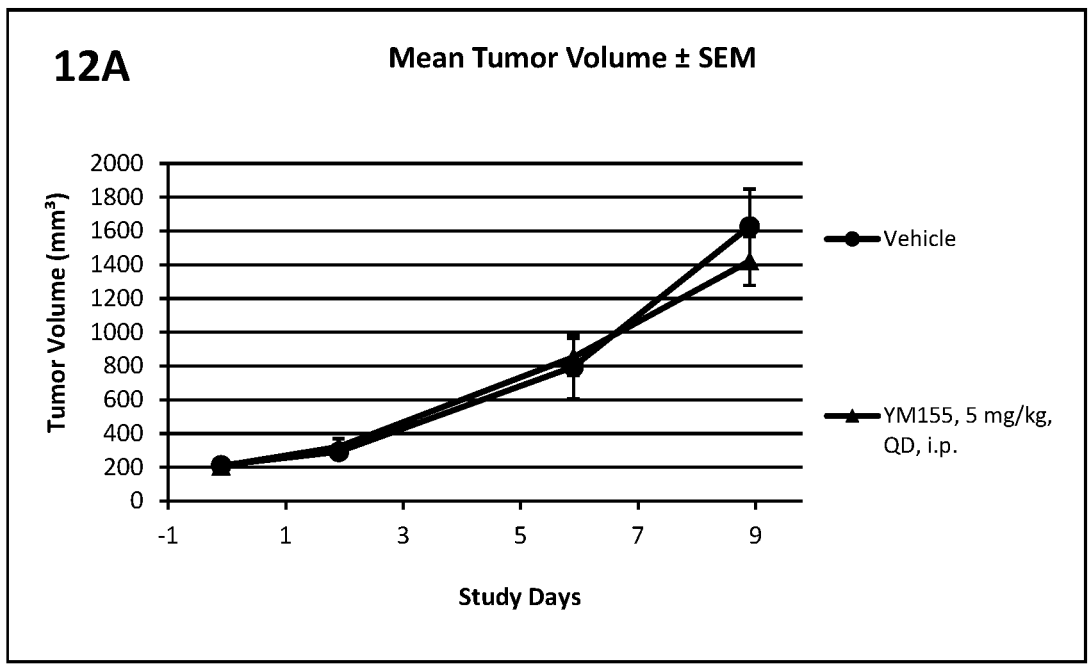
FIGS. 12A-12B show the antitumor effect of YM155 in U937 xenografts in mice.
Figure 12B:
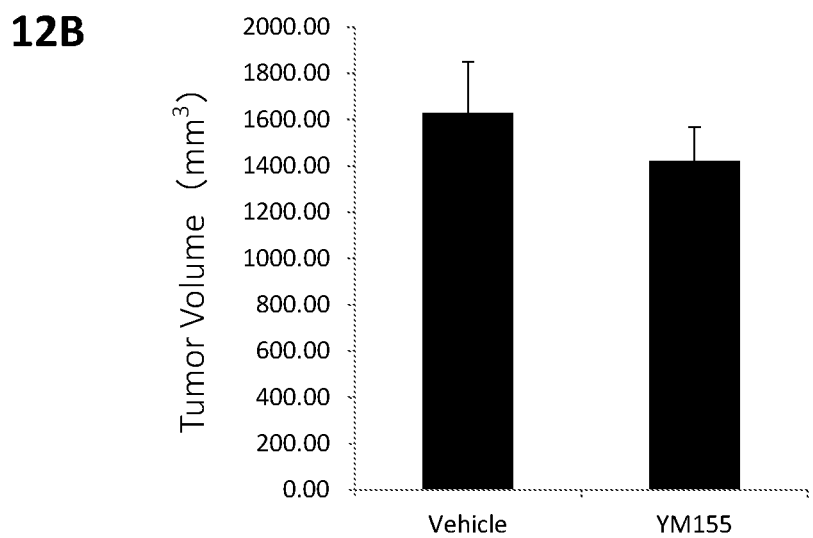
Figure 13A:
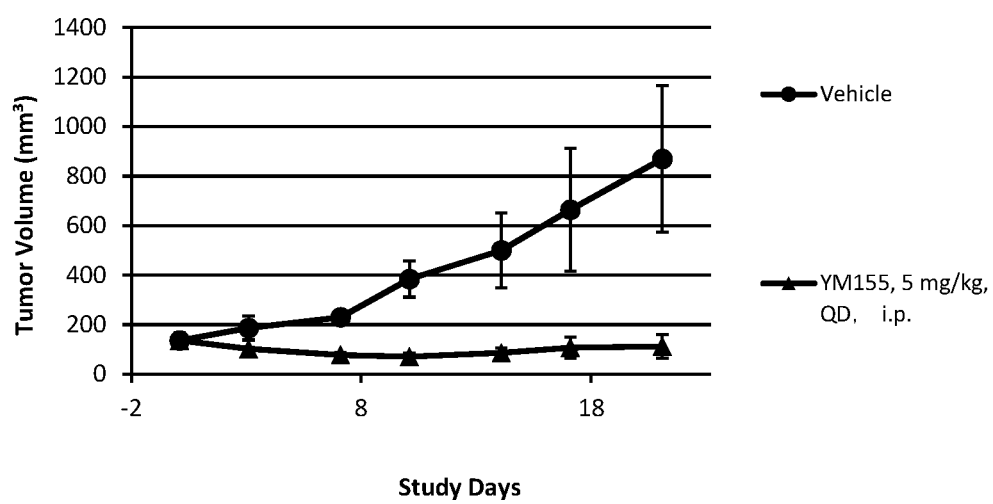
FIGS. 13A-13B show the antitumor effect of YM155 in IMR-32 xenografts in mice.
Figure 13B:
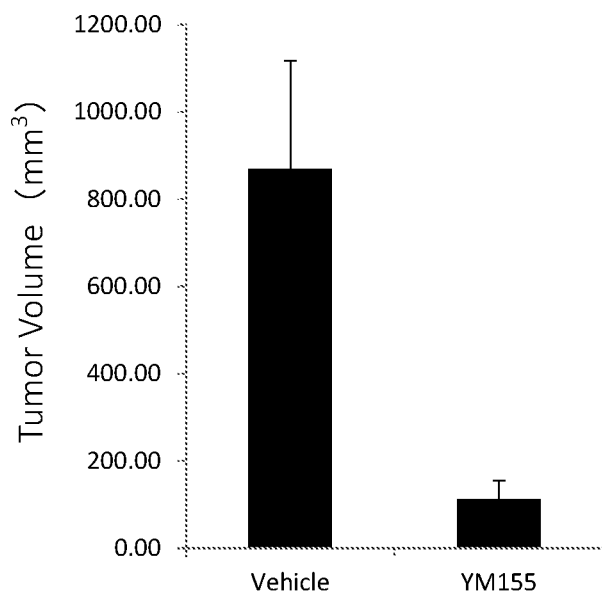
Figure 14A:
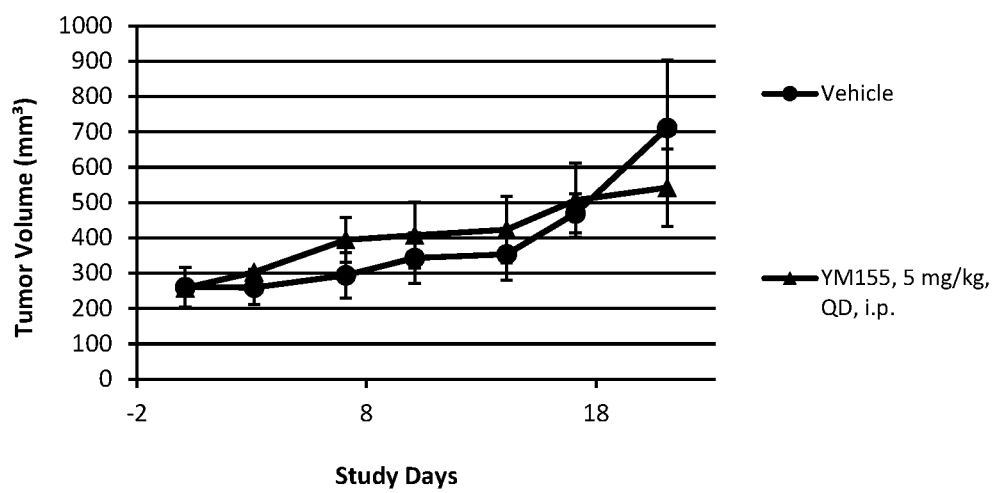
FIGS. 14A-14B show the antitumor effect of YM155 in SH-SY5Y xenografts in mice.
Figure 14B:
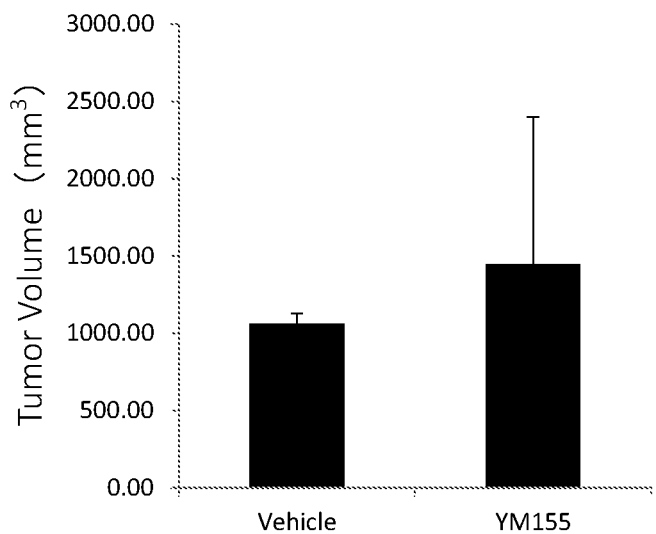

Examples of a "reference" (e.g., a MYC gene copy number "reference", a MYC gene chromosomal site "reference") include a value or amount or location obtained from a database, for example, a value or amount of a "wild-type" MYC gene copy number or a "wild-type" MYC gene chromosomal location site (see, e.g., FIG. 5 and FIG. 6 for a human MYCC gene chromosomal site reference; and FIG. 8 for a human MYCN gene chromosomal site reference). A "reference" also includes a value or amount or location obtained from a non-cancerous tissue from one or more controls, for example, one or more healthy or non-cancerous control subjects (e.g., a population of healthy or non-cancerous control subjects), or one or more corresponding non-cancerous control tissues from the subject being tested. Typically, a "corresponding" non-cancerous control tissue is obtained from the same type of tissue as the cancer tissue being tested. As with the cancer tissue, the MYC gene copy number reference from a non-cancerous control can be determined by any variety of methods, including, for example, by aCGH, SNP array, CNV sequence, and/or MLPA (supra). Similarly, the MYC gene chromosomal location site reference from a non-cancerous control can be determined by any variety of methods, including, for example, ISH, FISH, NGS, and/or CGH (supra).

In some embodiments, the sample of cancer tissue (or non-cancerous control tissue) is a surgical sample, a biopsy sample, a pleural effusion sample, or an ascetic fluid sample from the subject. Particular examples of samples of cancer tissues (or non-cancerous control tissues) include lung, blood, breast, gastrointestinal (stomach, colon, rectal), ovarian, pancreatic, liver, bladder, cervical, neuronal, uterine, salivary gland, kidney, prostate, thyroid, or muscle tissues. Certain embodiments include the step of obtaining the sample of cancer tissue (or non-cancerous control tissue) from the subject, for example, prior to determining MYC gene copy levels or MYC gene chromosomal location site.

In some embodiments, the subject is a human subject.

As noted above, certain embodiments include administering to the subject an anti-cancer agent excluding (or other than) YM155 monobromide if the subject is characterized as non-responsive to YM155 monobromide therapy, for example, if the MYC gene copy number in the cancer tissue is not substantially increased relative to that of the MYC gene copy number reference, or if the MYC gene chromosomal location site in the cancer tissue is not translocated relative to that of the MYC gene chromosomal location site reference. Exemplary anti-cancer agents (other than YM155 monobromide) for administering to a subject characterized as non-responsive to YM155 monobromide therapy include small molecules such as cytotoxic, chemotherapeutic, and anti-angiogenic agents, for instance, those that have been considered useful in the treatment of various cancers. General classes of anti-cancer agents include, without limitation, alkylating agents, anti-metabolites, anthracyclines, anti-tumor antibiotics, platinums, type I topoisomerase inhibitors, type II topoisomerase inhibitors, vinca alkaloids, and taxanes.

Specific examples of anti-cancer agents for administering to a subject characterized as non-responsive to YM155 monobromide therapy include chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, and paclitaxel, and pharmaceutically acceptable salts, acids or derivatives of any of the above. Additional examples of anti-cancer agents include imatinib, crizotinib, dasatinib, sorafenib, pazopanib, sunitinib, vatalanib, geftinib, erlotinib, AEE-788, dichloroacetate, tamoxifen, fasudil, SB-681323, and semaxanib (SU5416) (see Chico et al., Nat Rev Drug Discov. 8:829-909, 2009).

Further examples of anti-cancer agents for administering to a subject characterized as non-responsive to YM155 monobromide therapy include alkylating agents such as thiotepa, cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above.

Additional examples of anti-cancer agents for administering to a subject characterized as non-responsive to YM155 monobromide therapy include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Further examples of anti-cancer agents for administering to a subject characterized as non-responsive to YM155 monobromide therapy include anti-cancer antibodies such as 3F8, 8H9, abagovomab, adecatumumab, afutuzumab, alemtuzumab, alacizumab (pegol), amatuximab, apolizumab, bavituximab, bectumomab, belimumab, bevacizumab, bivatuzumab (mertansine), brentuximab vedotin, cantuzumab (mertansine), cantuzumab (ravtansine), capromab (pendetide), catumaxomab, cetuximab, citatuzumab (bogatox), cixutumumab, clivatuzumab (tetraxetan), conatumumab, dacetuzumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, taplitumomab (paptox), tenatumomab, teprotumumab, TGN1412, ticilimumab, tremelimumab, tigatuzumab, TNX-650, tositumomab, TRBS07, trastuzumab, tucotuzumab (celmoleukin), ublituximab, urelumab, veltuzumab, volociximab, votumumab, and zalutumumab. Also included are fragments, variants, and derivatives of these antibodies.

The methods described herein can be used in the treatment and/or diagnosis of any variety of cancers or tumors. In some embodiments, the cancer is a primary cancer, i.e., a cancer growing at the anatomical site where tumor progression began and yielded a cancerous mass. In some embodiments, the cancer is a secondary or metastatic cancer, i.e., a cancer which has spread from the primary site or tissue of origin into one or more different sites or tissues. In some instances, the cancer is selected from one or more of carcinoma, sarcoma such as rhabdomyosarcoma, for example, alveolar rhabdomyosarcoma (including sarcoma originating in the bones, tendons, cartilage, muscle, fat, fibrous, blood vessels, adipose, and/or connective tissue), neuroblastoma, medulloblastoma, astrocytoma, glioblastoma multiforme, retinoblastoma, myeloma, leukemia, lymphoma (including Hodgkin's lymphoma and Non-Hodgkin's lymphoma), adenosquamous carcinoma, carcinosarcoma, mixed mesodermal tumor, teratocarcinoma, lung cancer (including non-small cell lung cancer, small cell lung cancer, adenocarcinoma, and squamous carcinoma of the lung), breast cancer (including metastatic breast cancer), gastrointestinal cancer, stomach cancer, colorectal cancer, colon cancer, rectal cancer, ovarian cancer, pancreatic cancer, liver cancer, bladder cancer, cervical cancer, glioblastoma, uterine carcinoma, salivary gland carcinoma, kidney or renal cancer (e.g., Wilm's tumor), prostate cancer, thyroid cancer, and head and neck cancer.

In specific embodiments, the MYC gene is MYCC and the cancer is selected from lung cancers and blood cancers, optionally leukemias and lymphomas. In specific embodiments, the MYC gene is MYCN and the cancer is selected from neuroblastoma, small cell lung cancer, prostate cancer, alveolar rhabdomyosarcoma, medulloblastoma, glioblastoma multiforme, retinoblastoma, and breast cancer.

In some embodiments, as noted above, the cancer or tumor is a metastatic cancer. Further to the above cancers, exemplary metastatic cancers include, without limitation, bladder cancers which have metastasized to the bone, liver, and/or lungs; breast cancers which have metastasized to the bone, brain, liver, and/or lungs; colorectal cancers which have metastasized to the liver, lungs, and/or peritoneum; kidney cancers which have metastasized to the adrenal glands, bone, brain, liver, and/or lungs; lung cancers which have metastasized to the adrenal glands, bone, brain, liver, and/or other lung sites; melanomas which have metastasized to the bone, brain, liver, lung, and/or skin/muscle; ovarian cancers which have metastasized to the liver, lung, and/or peritoneum; pancreatic cancers which have metastasized to the liver, lung, and/or peritoneum; prostate cancers which have metastasized to the adrenal glands, bone, liver, and/or lungs; stomach cancers which have metastasized to the liver, lung, and/or peritoneum; thyroid cancers which have metastasized to the bone, liver, and/or lungs; and uterine cancers which have metastasized to the bone, liver, lung, peritoneum, and/or vagina; among others.

In certain embodiments, the methods described herein are sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, the methods described are sufficient to result in stable disease. In certain embodiments, the methods described herein are sufficient to result in clinically relevant reduction in symptoms of a particular disease indication known to the skilled clinician.

The methods for treating cancers can be combined with other therapeutic modalities. For example, a combination therapy described herein can be administered to a subject before, during, or after other therapeutic interventions, including symptomatic care, radiotherapy, surgery, transplantation, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

Methods for identifying subjects with one or more of the diseases or conditions described herein are known in the art.

For in vivo use, for instance, for the treatment of human disease or testing, the agents described herein are generally incorporated into one or more therapeutic or pharmaceutical compositions prior to administration.

To prepare a therapeutic or pharmaceutical composition, an effective or desired amount of one or more agents is typically mixed with any pharmaceutical carrier(s) or excipient known to those skilled in the art to be suitable for the particular agent and/or mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of agents described herein, in pure form or in an appropriate therapeutic or pharmaceutical composition, can be carried out via any of the accepted modes of administration of agents for serving similar utilities. The therapeutic or pharmaceutical compositions can be prepared by combining an agent-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, intradermal, intramuscular, subcutaneous or topical. Preferred modes of administration depend upon the nature of the condition to be treated or prevented. Particular embodiments include administration by IV infusion.

Carriers can include, for example, pharmaceutically- or physiologically-acceptable carriers, excipients, or stabilizers that are non-toxic to the cell or mammal being exposed thereto at the dosages and concentrations employed. Often the physiologically-acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more agents can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related therapeutic or pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Therapeutic or pharmaceutical compositions according to certain embodiments of the present disclosure are formulated so as to allow the active ingredients contained therein to be bioavailable upon administration of the composition to a subject or patient. Compositions that will be administered to a subject or patient may take the form of one or more dosage units, where for example, a tablet may be a single dosage unit, and a container of a herein described agent in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will typically contain a therapeutically effective amount of an agent described herein, for treatment of a disease or condition of interest.

A therapeutic or pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid. Certain embodiments include sterile, injectable solutions.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The therapeutic or pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid therapeutic or pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid therapeutic or pharmaceutical composition intended for either parenteral or oral administration should contain an amount of an agent such that a suitable dosage will be obtained. Typically, this amount is at least 0.01% of the agent of interest in the composition. When intended for oral administration, this amount may be varied to be between 0.1 and about 70% of the weight of the composition. Certain oral therapeutic or pharmaceutical compositions contain between about 4% and about 75% of the agent of interest. In certain embodiments, therapeutic or pharmaceutical compositions and preparations according to the present invention are prepared so that a parenteral dosage unit contains between 0.01 to 10% by weight of the agent of interest prior to dilution.

The therapeutic or pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The therapeutic or pharmaceutical compositions in solid or liquid form may include a component that binds to agent and thereby assists in the delivery of the compound. Suitable components that may act in this capacity include monoclonal or polyclonal antibodies, one or more proteins or a liposome.

The compositions described herein may be prepared with carriers that protect the agents against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The therapeutic or pharmaceutical compositions may be prepared by methodology well known in the pharmaceutical art. For example, a therapeutic or pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the agent so as to facilitate dissolution or homogeneous suspension of the agent in the aqueous delivery system.

Certain embodiments include the use of a diagnostic kit for determining or predicting a therapeutic response (or responsiveness) to YM155 monobromide [1-(2-Methoxyethyl)-2-methyl-4,9-dioxo-3-(pyrazin-2-ylmethyl)-4,9-dihydro-1H- naphtho[2,3-d]imidazolium bromide] therapy in a subject with cancer, comprising means for measuring MYC gene copy number, or MYC gene chromosomal location site, in a sample of tissue from the subject, including cancer tissue and non-cancerous tissue. Also included are patient care kits, comprising: (a) means for measuring MYC gene copy number, or MYC gene chromosomal location site, in a sample of tissue from a subject, including cancer tissue and non-cancerous tissue; and (b) YM155 monobromide [1-(2-Methoxyethyl)-2-methyl-4,9-dioxo-3-(pyrazin-2-ylmethyl)-4,9-dihydro-1H-naphtho[2,3-d]imidazolium bromide].

In some embodiments, the means for measuring MYC gene copy number comprise reagents for performing a diagnostic assay selected from one or more of array comparative genome hybridization (aCGH), single nucleotide polymorphism (SNP) array, copy number variation (CNV) sequencing, and multiplex ligation-dependent probe amplification (MLPA) on a human MYC gene. In some embodiments, the means for measuring MYC gene chromosomal location site comprise reagents for performing a diagnostic assay selected from one or more of in situ hybridization (ISH), fluorescence in situ hybridization (FISH), next generation sequencing (NGS), and comparative genome hybridization (CGH) on a human MYC gene.

Certain diagnostic or patient care kits include a MYC gene copy number reference value obtained from a database, or determined from a non-cancerous tissue from a control. Some diagnostic or patient care kits include a MYC gene chromosomal location site reference obtained from a database, or determined from a non-cancerous tissue from a control. The kits can also include written instructions, for example, on how to determine MYC gene copy number and/or a MYC gene chromosomal location site in a sample of cancer tissue from a subject, and/or from a non-cancerous control.

In some embodiments, a diagnostic or patient care kit contains separate containers, dividers, or compartments for the composition(s) and informational material(s). For example, the composition(s) or reagents can be contained in a bottle, vial, or syringe, and the informational material(s) can be contained in association with the container. In some embodiments, the separate elements of the kit are contained within a single, undivided container. For example, the composition(s) or reagents are contained in a bottle, vial or syringe that has attached thereto the informational material in the form of a label. In some embodiments, the kit includes a plurality (e.g., a pack) of individual containers, each containing one or more compositions, reagents, and/or unit dosage forms of YM155 monobromide. For example, the kit includes a plurality of syringes, ampules, foil packets, or blister packs, each containing a reagent or a single unit dose of YM155 monobromide. The containers of the kits can be air tight, waterproof (e.g., impermeable to changes in moisture or evaporation), and/or light-tight.

The patient care kit optionally includes a device suitable for administration of the agent(s), e.g., a syringe, inhalant, dropper (e.g., eye dropper), swab (e.g., a cotton swab or wooden swab), or any such delivery device. In some embodiments, the device is an implantable device that dispenses metered doses of the agent(s). Also included are methods of providing a kit, e.g., by combining the components described herein.

In certain aspects, the diagnostic or therapeutic response tests or methods described herein are performed at a diagnostic laboratory, and the results are then provided to the subject, or to a physician or other healthcare provider that plays a role in the subject's healthcare and cancer treatment. Particular embodiments thus include methods for providing the results of the responsiveness test to the subject in need thereof, or to the physician or other healthcare provider. These results or data can be in the form of a hard-copy or paper-copy, or an electronic form, such as a computer-readable medium.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill certain changes and modifications may be made thereto without departing from the spirit or scope of the description or appended claims. The following examples are provided by way of illustration only and not by way of limitation. Those of skill in the art will readily recognize a variety of noncritical parameters that could be changed or modified to yield essentially similar results.

EXAMPLES

Example 1

Efficacy of YM155 Monobromide in Cancer Cell Lines

Studies were performed to evaluate the efficacy of YM155 monobromide in various cancer cell lines, and also to correlate the efficacy of YM155 monobromide to MYC gene copy number.

Lung Cell Culture Human lung cancer cell line NCI-H1975, HCC827, NCI-H226 and HCC4006 cells were cultured in RPMI 1640 (Hyclone™, SH30809.01B) supplemented with 10% fetal bovine serum (GEMINI, 900-108). Cultures were incubated at 37° C. in 5% $CO_2$. NCI-H1975, HCC827 and NCI-H226 were purchased from Cell Bank, Shanghai Institutes for Biological Sciences, Chinese Academy of Sciences. HCC4006 was purchased from CoBioer Biosciences Corporation (Nanjing, China).

Cell Treatment and proliferation assay. NCI-H1975, HCC827, NCI-H226 and HCC4006 cell were seeded in 96-well plates (Corning-Costar, 3603) at 2000 cells/well in 200 µl culture medium for 24 hours, respectively. Then cells were treated with YM155 (50, 30, 20, 10, 2, 0.4, 0.08, 0.016 and 0.0032 nM; APExBIO, A4221) or DMSO (0.1%; Amresco, 67-68-5). After 72 hour incubation, cells were labeled with 5-Ethynyl-2'-deoxyuridine (EdU, final concentration at 1 uM; Sigma, 900584) for additional 4 h under the same culture condition.

After incubation with EdU, cells were fixed with formaldehyde (final concentration at 4%; Thermo, 28908) for 30 min at room temperature. The cells were washed twice with PBS (Hyclone™, SH30256.01) and then permeabilized with 0.5% Triton X-100 (T8787-250 ML) in PBS overnight at 4° C. After discarding the supernatant, the cells were incubated with Hoechst 33342 (Invitrogen, H1399) for 1 hour at room temperature and then washed again twice with PBS.

Cells were incubated with staining mix (Beijing Percans Oncology Medical Research Co., Ltd., RUO-00401#150T) for 30 min at room temperature and then washed three times with PBS. The cells were kept in PBS and protected from light throughout experiments.

High content imaging analysis. The treated cells were scanned for image acquisition with CellInsight™ CX5 High-Content Screening (HSC) Platform (Thermo Fisher) that was equipped with filters for Hoechst 33342 (Ex: 386 nm) and EdU (Ex: 560 nm). The total cell count and EdU-positive cell count were analysis by measuring the signal intensity in the nuclear region.

Figure 2:
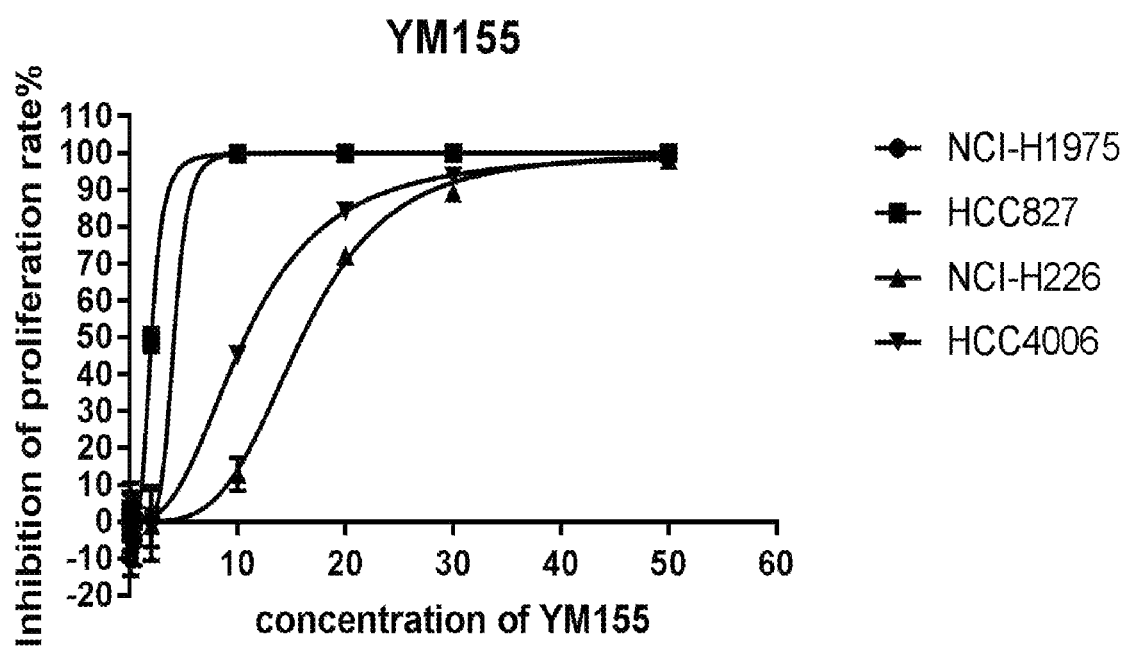
FIG. 2 shows that YM155 inhibits cell proliferation of human lung cancer cell line. NCI-H1975, HCC827, NCI-H226, and HCC4006 cells were cultured in 96-well plates and treated with YM155 at indicated dose (nM). Cell proliferation was detected by EdU proliferation assay. The data presented is mean±SEM.

As shown in FIG. 2, YM155 inhibits cell proliferation of human lung cancer cell lines. NCI-H1975, HCC827, NCI-H226, and HCC4006 were exposed to different concentrations of YM155 for 72 hours. However, the proliferation inhibitory effects of YM155 were different in these cell lines, with the calculated $IC_{50}$ showed in Table E1 below. NCI-H1975 and HCC827 with MYC gene amplification (increased MYC gene copy number relative to a reference) were significantly more sensitive to YM155 than NCI-H226 and HCC4006 without MYC gene amplification.

TABLE E1

MYCC Gene Copy Number and YM155 $IC_{50}$ in Human Lung Cancer Cell Lines

|  | NCI-H1975 | HCC827 | NCI-H226 | HCC4006 |
| --- | --- | --- | --- | --- |
| Copy Number | 12.1 | 6.44 | 2.93 | 2.25 |
| Expression | 7.64 | 7.2 | 6.39 | 2.78 |
| YM155 $IC_{50}$ (nm) | 4.122 | 2.015 | 15.99 | 10.73 |

Blood Cell Culture Human acute myeloid leukemia cells (U937 and HL-60) and Human Burkitt's lymphoma cells (Ramos) were cultured in RPMI 1640 supplemented with 10% fetal bovine serum. Cultures were incubated at 37° C., in 5% $CO_2$. U937 and HL-60 cells were purchased from Cell Bank, Shanghai Institutes for Biological Sciences, Chinese Academy of Sciences. Ramos cells were purchased from CoBioer Biosciences Corporation (Nanjing, China). Ramos cells carry the IgH-c-MYC translocation mutation.

Cell Treatment and proliferation assay. U937, HL-60, and Ramos cells were seeded in 96-well plates (Corning-Costar, 3599) at 40000 cells/well in 200 µl culture medium treated with YM155 (200, 100, 50, 25, 12.5, 2.5, 1, 0.5 nM; APExBIO, A4221) or DMSO (0.1%; Amresco, 67-68-5). After 72 hour incubation, cell proliferation was measured by XTT assay (Cell Proliferation Kit II XTT, Sigma, 11465015001) according to manufacturer's protocols. Briefly, after YM155 treatment, 50 µl of the XTT labeling mixture was added to each well, followed by incubation of the microplate for 4 hours in a humidified atmosphere. The absorbance of wavelength at 490 nm ($OD_{490}$) and 650 nm ($OD_{650}$) was determined respectively by SpectraMax 190. The $IC_{50}$ was calculated by the value of $OD_{490}$-$OD_{650}$.

Figure 3:
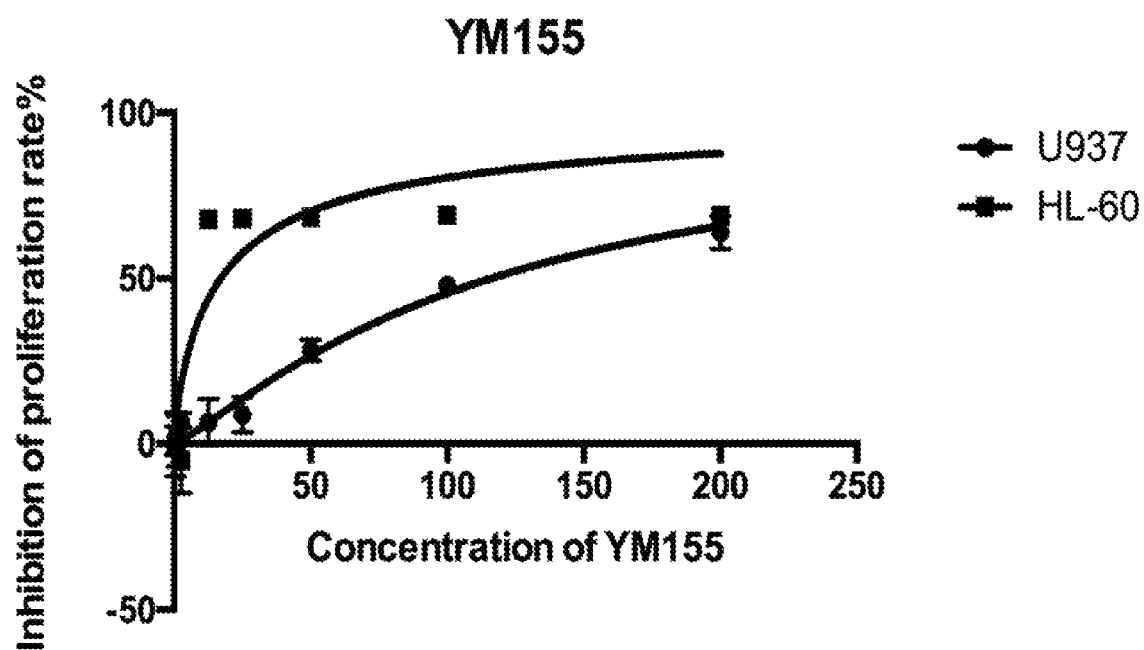
FIG. 3 shows that YM155 inhibits cell proliferation of human acute myeloid leukemia (AML) cell line. U937 and HL-60 cells were cultured in 96-well plates and treated with YM155 at indicated dose (nM). Cell proliferation was detected by XTT cell viability assay. The data presented is mean±SEM.
Figure 4:
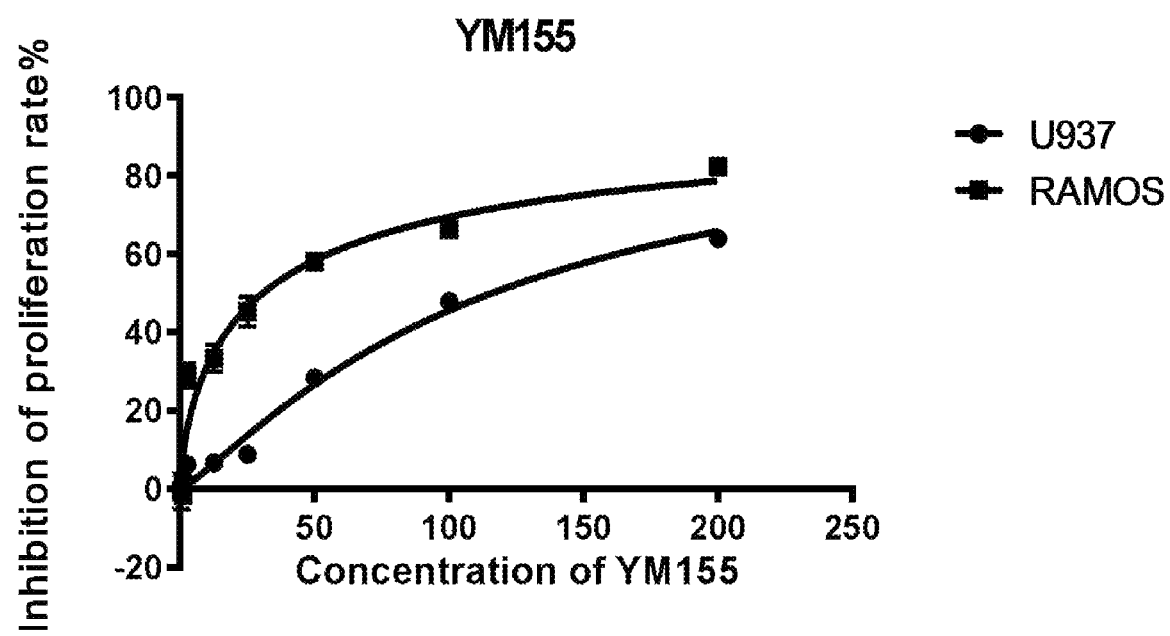
FIG. 4 shows that YM155 inhibits cell proliferation of U937 and RAMOS cell line. U937 and RAMOS cells were cultured in 96-well plates and treated with YM155 at indicated dose (nM). Cell proliferation was detected by XTT cell viability assay. The data presented is mean±SEM.

As shown in FIG. 3 and FIG. 4, YM155 inhibits cell proliferation of human acute myeloid leukemia cells and Human Burkitt's lymphoma cells. U937, HL-60, and Ramos were exposed to different concentrations of YM155 for 72 hours. However, the proliferation inhibitory effects of YM155 were different in these cell lines, with the calculated $IC_{50}$ showed in Table E2 below 5. HL-60 cells with MYC gene amplification (increased MYC gene copy number relative to a reference) and Ramos cells with MYC gene translocation were more sensitive to YM155 than U937 cells without MYC gene amplification or translocation.

TABLE E2

MYCC Gene Copy Number and YM155 $IC_{50}$ in Leukemia/Lymphoma Cell Lines

|  | U937 | HL-60 | Ramos |
|---|---|---|---|
| Copy Number | 2.39 | 9.6 | IgH/c-MYC translocation |
| Expression | 8.22 | 9.35 | translocation |
| YM155 $IC_{50}$ (nm) | 116 | 17.07 | 30.83 |

Neuroblastoma Cell Culture. Neuroblastoma cell lines IMR-32, NB-1, KP-N-YN, SK-N-BE, SK-N-SH, and SH-SY56Y cells were cultured in 96-well plates and treated with YM155 at indicated doses (nM). Human neuroblastoma cell line IMR-32 was cultured in MEM (Hyclone™, SH30024.01) supplemented with 10% fetal bovine serum (GEMINI, 900-108); neuroblastoma cell lines NB-1 and KP-N-YN were cultured in RPMI 1640 (Hyclone™, SH30809.01B) supplemented with 10% fetal bovine serum; neuroblastoma cell line SK-N-BE was cultured in F12 (Gibco, 11765-054)/MEM(1:1) (Hyclone™, SH30024.01) supplemented with 10% fetal bovine serum; neuroblastoma cell line SH-SY5Y was cultured in in MEM/F12(1:1) supplemented with 10% fetal bovine serum; and neuroblastoma cell line SK-N-SH was cultured in MEM supplemented with 10% fetal bovine serum. Cultures were incubated at 37° C., in 5% CO2.

IMR-32, SH-SY56Y, and SK-N-SH were purchased from Cell Bank, Shanghai Institutes for Biological Sciences, Chinese Academy of Sciences. NB-1, KP-N-YN and SK-N-BE cells were purchased from CoBioer Biosciences Corporation (Nanjing, China).

Cell Treatment and proliferation assay. IMR-32, SH-SY5Y, SK-N-SH, NB-1, KP-N-YN, and SK-N-BE cells were seeded in 96-well plates (Corning-Costar, 3603) at 2000 cells/well in 200 μl culture medium for 24 hours. Cells were then treated with YM155 (200, 100, 50, 25, 12.5, 6.25, 3.125, 1.5625 and 0.78125 nM; APExBIO, A4221) or DMSO (0.1%; Amresco, 67-68-5). After 72 hour incubation, cells were labeled with 5-Ethynyl-2'-deoxyuridine (EdU, final concentration at 1 uM; Sigma, 900584) for additional 4 hours under the same culture condition.

After incubation with EdU, cells were fixed with Formaldehyde (final concentration at 4%; Thermo, 28908) for 30 min at room temperature. The cells were washed twice with PBS (Hyclone™, SH30256.01), then permeabilized with 0.5% Triton X-100 (T8787-250 ML) in PBS overnight at 4° C. After discarding the supernatant, the cells were incubated with Hoechst 33342 (Invitrogen, H1399) for 1 hour at room temperature, then washed again twice with PBS. Cells were incubated with staining mix (Beijing Percans Oncology Medical Research Co., Ltd., RUO-00401#150T) for 30 minutes at room temperature, then washed the cells three times with PBS. The cells were kept in PBS and protected from light throughout experiments.

High content imaging analysis. The treated cells were scanned for image acquisition with CellInsight™ CX5 High-Content Screening (HSC) Platform (Thermo Fisher), equipped with filters for Hoechst 33342 (Ex: 386 nm) and EdU (Ex: 560 nm). The total cell count and EdU-positive cell count were analysis by measuring the signal intensity in the nuclear region.

Figure 7:
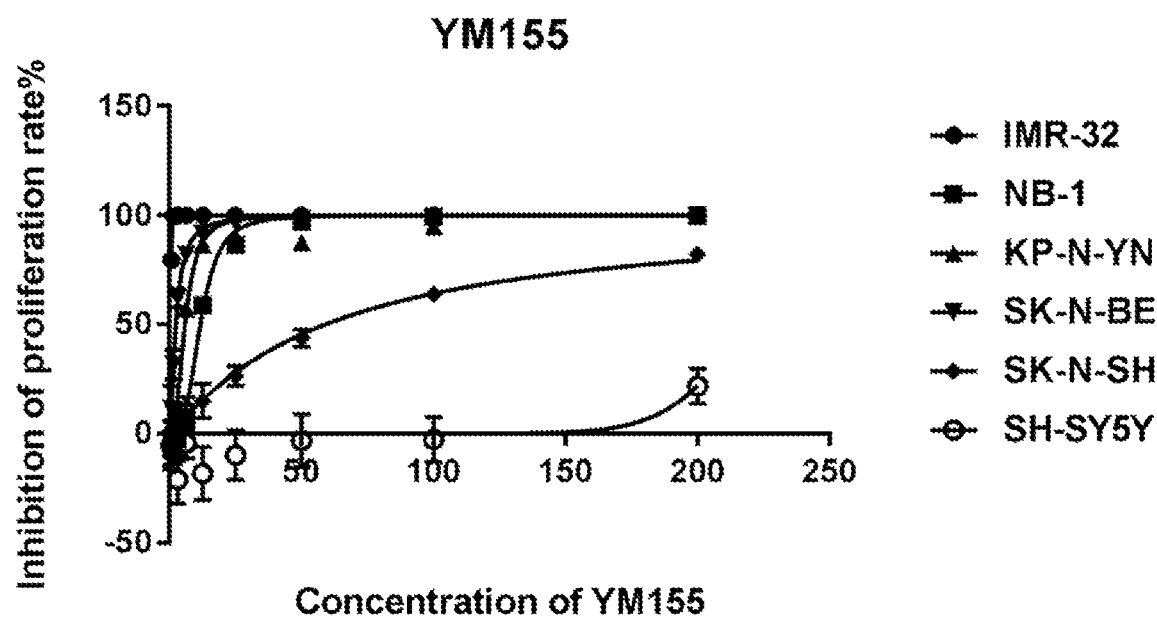
FIG. 7 shows that YM155 inhibits cell proliferation of human neuroblastoma cell lines, especially cell lines characterized by increased copy number of N-MYC (see also Table E3). Cell proliferation was detected by EdU assay. The data presented is mean±SD.

As shown in FIG. 7 and Table E3 below, YM155 inhibits cell proliferation of neuroblastoma cell lines. It is especially effective at inhibiting cell proliferation of the IMR-32, NB-1, KP-N-YN, and SK-N-BE neuroblastoma cell lines, which are characterized by increased copy number of NMYC.

TABLE E3

MYCN Gene Copy Number and YM155 in Neuroblastoma Cell Lines

|  | IMR-32 | NB-1 | KP-N-YN | SK-N-BE | SK-N-SH | SH-SY5Y |
|---|---|---|---|---|---|---|
| Copy Number | 16.4 | 26 | 22.88 | 19.57 | 2.8 | 2.9 |
| Expression | 8.5 | 8.5 | 9.55 | 10.14 | 4.09 | 4.25 |
| YM155 $IC_{50}$ (nm) | 0.62 | 11.71 | 5.89 | 2.46 | 59.06 | >220 |

These data illustrate that MYC gene amplification (i.e., increased MYC gene copy number relative to a reference) and MYC gene translocation can be used to predict responsiveness to YM155 monobromide therapy in cancer, including lung cancers, blood cell cancers, neuroblastomas, and others.

Example 2

HCC827/HCC 4006 Xenograft Experiment

Four to six weeks-old female mice (Balb/C-nu) were purchased from BEIJING HFK BIOSCIENCE Co., Ltd. Cell suspensions (HCC827 (epithelial lung adenocarcinoma): $5 \times 10^6/0.1$ ml per mouse; HCC4006: $5 \times 10^6/0.1$ ml per mouse) of cell culture medium were inoculated subcutaneously into the right flank of the mice. When tumor size reached around 100 mm$^3$-150 mm$^3$, mice were randomized into treatment and control groups. YM155 (Biochem partner, BCP01864) at 5 mg/kg or vehicle (Saline, Shijiazhuang No. 4 Pharmaceutical) was administered subcutaneously once daily for five days/week over three weeks. Body weight of mice was assessed twice weekly, and tumor diameter (long diameter and short diameter) was measured using standard calipers. The tumor volume=½*long diameter*(short diameter)$^2$. After two or three weeks observation, mice were sacrificed for analysis. The data are presented in FIGS. 9A-9B and FIGS. 10A-10B.

Example 3

RAMOS/U937 Xenograft Experiments

Four to six weeks-old female mice (RAMOS: SCID; U937: NOD/SCID) were purchased from BEIJING HFK BIOSCIENCE Co., Ltd. Cell suspensions (RAMOS: $1 \times 10^7/0.1$ ml per mouse; U937: $2 \times 10^6/0.1$ ml+0.1 ml matrigel per mouse) of cell culture medium were inoculated subcutaneously into the right flank of the mice. When tumor size reached around 100 mm$^3$-150 mm$^3$, mice were randomized into treatment and control groups. YM155 (Biochem partner, BCP01864) at 5 mg/kg or vehicle (Saline, Shijiazhuang No. 4 Pharmaceutical) was administered subcutaneously once daily for nine days. Body weight of mice was assessed twice weekly, and tumor diameter (long diameter and short diameter) was measured using standard calipers. The tumor volume=½*long diameter*(short diameter)$^2$. After two or three weeks observation, mice were sacrificed for analysis. The data are presented in FIGS. 11A-11B and FIGS. 12A-12B.

Example 6

IMR-3/SH-SY5Y Xenograft Experiments

Four to six weeks-old female mice (IMR-32: NOD/SCID; SH-SY5Y: Balb/C-nu) were purchased from BEIJING HFK BIOSCIENCE Co., Ltd. Cell suspensions (IMR-32: $5 \times 10^6$/0.1 ml+0.1 ml matrigel per mouse; SH-SY5Y: $2 \times 10^6$/0.1 ml+0.1 ml matrigel per mouse) of cell culture medium were inoculated subcutaneously into the right flank of the mice. When tumor size reached around 100 mm$^3$-150 mm$^3$, mice were randomized into treatment and control groups. YM155 (Biochem partner, BCP01864) at 5 mg/kg or vehicle (Saline, Shijiazhuang No. 4 Pharmaceutical) was administered subcutaneously once daily for five days/week over 3 weeks. Body weight of mice was assessed twice weekly, and tumor diameter (long diameter and short diameter) was measured using standard calipers. The tumor volume=½*long diameter*(short diameter)$^2$. After two or three weeks observation, mice were sacrificed for analysis. The data are presented in FIGS. 13A-13B and FIGS. 14A-14B.

The invention claimed is:

1. A method for treating cancer in a subject in need thereof, comprising:
    (a) determining MYCC gene chromosomal location site in a sample of cancer tissue from the subject; and
    (b) administering YM155 monobromide [1-(2-Methoxyethyl)-2-methyl-4,9-dioxo-3-(pyrazin-2-ylmethyl)-4,9-dihydro-1H-naphtho[2,3-d]imidazolium bromide], to the subject if MYCC gene chromosomal location site in the cancer tissue is translocated relative to that of a MYCC gene chromosomal location site reference, thereby treating cancer in the subject in need thereof, wherein the cancer is a lymphoma.

2. The method of claim 1, comprising determining MYCC gene chromosomal location site in the cancer tissue by in situ hybridization (ISH), fluorescence in situ hybridization (FISH), next generation sequencing (NGS), or comparative genome hybridization (CGH).

3. The method of claim 1, comprising obtaining the MYCC gene chromosomal location site reference from a database, or determining the MYCC gene chromosomal location site reference from a non-cancerous tissue from a control, optionally by ISH, FISH, NGS, or CGH.

4. The method of claim 1, comprising obtaining the sample of cancer tissue from the subject.

5. The method of claim 1, wherein the sample of cancer tissue is a surgical sample, a biopsy sample, a pleural effusion sample, or an ascetic fluid sample obtained from the subject, optionally blood.

6. The method of claim 1, wherein the subject is a human subject.

7. The method of claim 1, wherein the cancer is Burkitt's lymphoma.

8. A method for predicting therapeutic response to YM155 mono bromide [1-(2-Methoxyethyl)-2-methyl-4,9-dioxo-3-(pyrazin-2-ylmethyl)-4,9-dihydro-1H-naphtho[2,3-d]imidazolium bromide], in a subject with cancer, comprising
    (a) determining MYCC gene chromosomal location site in a sample of cancer tissue from the subject; and
    (b) (1) characterizing the subject as responsive to YM155 monobromide therapy if the MYCC gene chromosomal location site in the cancer tissue is translocated relative to that of a MYCC gene chromosomal location site reference; or
        (ii) characterizing the subject as non-responsive to YM155 monobromide therapy if the MYCC gene chromosomal location site in the cancer tissue is not translocated relative to that of the MYCC gene chromosomal location site reference,
    thereby predicting therapeutic response to YM155 monobromide in the subject with cancer, wherein the cancer is a lymphoma.

9. The method of claim 8, comprising administering YM155 monobromide to the subject if the subject is characterized as responsive to YM155 monobromide therapy.

* * * * *

UNITED STATES PATENT AND TRADEMARK OFFICE
CERTIFICATE OF CORRECTION

| | | |
|---|---|---|
| PATENT NO. | : 12,163,193 B2 | Page 1 of 1 |
| APPLICATION NO. | : 17/268042 | |
| DATED | : December 10, 2024 | |
| INVENTOR(S) | : Xiang Li et al. | |

It is certified that error appears in the above-identified patent and that said Letters Patent is hereby corrected as shown below:

On the Title Page

Item [30]:
"Nov 6, 2018" should read -- Nov 16, 2018 --

In the Claims

Column 24, Claim 8, Line 19:
"mono bromide" should read -- monobromide --

Column 24, Claim 8, Line 24:
"(b) (1)" should read -- (b) (i) --

Signed and Sealed this
Twenty-first Day of January, 2025

Coke Morgan Stewart
*Acting Director of the United States Patent and Trademark Office*